United States Patent
Lebner et al.

(10) Patent No.: US 8,105,353 B2
(45) Date of Patent: *Jan. 31, 2012

(54) WOUND CLOSURE KIT AND METHOD OF USING THE SAME

(75) Inventors: Michael Lebner, Wellesley Hills, MA (US); Raymond Barbuto, Dagsboro, DE (US)

(73) Assignee: Clozex Medical, LLC, Wellesley, MA (US)

( * ) Notice: Subject to any disclaimer, the term of this patent is extended or adjusted under 35 U.S.C. 154(b) by 1261 days.

This patent is subject to a terminal disclaimer.

(21) Appl. No.: 11/242,733

(22) Filed: Oct. 4, 2005

(65) Prior Publication Data

US 2007/0038247 A1 Feb. 15, 2007

Related U.S. Application Data

(63) Continuation-in-part of application No. 11/200,423, filed on Aug. 9, 2005.

(51) Int. Cl.
 *A61D 1/00* (2006.01)
(52) U.S. Cl. .................................. 606/215; 606/213
(58) Field of Classification Search .......... 606/216, 606/213, 215; 602/41, 42, 43, 48, 52–59
 See application file for complete search history.

(56) References Cited

U.S. PATENT DOCUMENTS

| | | | |
|---|---|---|---|
| 24,906 A | 7/1859 | Goodfellow | |
| 1,074,413 A | 1/1913 | De Baun et al. | |
| 1,230,444 A | 6/1917 | Teed | |
| 1,969,188 A | 10/1932 | Spicer | |
| 2,196,296 A | 5/1940 | Flynn | |
| 2,387,131 A * | 10/1945 | Fernandez | 606/216 |
| 2,532,011 A | 11/1950 | Dahlquist et al. | |
| 2,818,865 A | 9/1953 | Jacoby, Jr. | |
| 2,762,371 A | 9/1956 | Guio | |
| RE24,906 E | 12/1960 | Ulrich | |

(Continued)

FOREIGN PATENT DOCUMENTS

GB 1299367 12/1972

(Continued)

OTHER PUBLICATIONS

Packaging and instruction sheet for "umbillical hernia plaster" produced by Lohmann GmbH & Co., KG (Postflach 23 43, D-56513 Neuwied, Germany); undated.

(Continued)

*Primary Examiner* — Corrine M McDermott
*Assistant Examiner* — Christina Lauer
(74) *Attorney, Agent, or Firm* — Pierce Atwood, LLP; Kevin M. Farrell, Esq.; Katherine A. Wrobel, Esq.

(57) ABSTRACT

The present invention includes a first and a second interlaced component, each having a permeable adhesive-backed wound edge pad for attachment to the skin of a patient adjacent to a laceration or incision to be closed. Each of the permeable wound edge pads is attached to an opposing tension adjusting pad that also has an adhesive backing. The wound edge pads are connected to the respective tension adjusting pads by elongate connecting elements that may be flat or tubular in shape. The present invention also includes an adhesive that may be applied in liquid form to the permeable wound edge pads. Adhesion of the adhesive on and within the permeable wound edge pads seals the wound site and adds structural rigidity to the interlaced components.

29 Claims, 16 Drawing Sheets

U.S. PATENT DOCUMENTS

| | | |
|---|---|---|
| 3,020,186 A | 2/1962 | Lawrence |
| 3,329,548 A | 7/1967 | Blatz |
| 3,389,827 A | 6/1968 | Abere |
| 3,645,835 A | 2/1972 | Hodgson |
| 4,112,213 A | 9/1978 | Waldman |
| 4,141,363 A | 2/1979 | James et al. |
| 4,310,509 A | 1/1982 | Berglund et al. |
| 4,323,557 A | 4/1982 | Rosso et al. |
| 4,328,057 A | 5/1982 | Gutow |
| 4,374,520 A | 2/1983 | Grossmann |
| 4,413,621 A | 11/1983 | McCracken |
| 4,423,731 A | 1/1984 | Roomi |
| 4,472,480 A | 9/1984 | Olson |
| 4,485,809 A | 12/1984 | Dellas |
| 4,499,896 A | 2/1985 | Heinecke |
| RE31,887 E | 5/1985 | Hodgson |
| 4,524,095 A | 6/1985 | Gockel et al. |
| 4,545,371 A | 10/1985 | Grossmann |
| 4,549,063 A | 10/1985 | Ang |
| 4,587,146 A | 5/1986 | Anhauser |
| 4,590,022 A | 5/1986 | Cioca |
| 4,595,001 A | 6/1986 | Potter |
| 4,595,011 A | 6/1986 | Phillips |
| 4,596,738 A | 6/1986 | Metcalfe |
| 4,600,001 A | 7/1986 | Gilman |
| 4,614,183 A | 9/1986 | McCracken |
| 4,646,731 A | 3/1987 | Brower |
| 4,664,106 A | 5/1987 | Snedeker |
| 4,678,462 A | 7/1987 | Vaillancourt |
| 4,706,662 A | 11/1987 | Thompson |
| 4,737,410 A | 4/1988 | Kantner |
| 4,753,232 A | 6/1988 | Ward |
| 4,787,380 A | 11/1988 | Scott |
| 4,825,866 A | 5/1989 | Pierce |
| 4,926,850 A | 5/1990 | Lott et al. |
| 4,950,282 A | 8/1990 | Beisang |
| RE33,353 E | 9/1990 | Heinecke |
| RE33,727 E | 10/1991 | Sims |
| 5,088,483 A | 2/1992 | Heinecke |
| 5,106,383 A | 4/1992 | Mulder |
| 5,135,518 A | 8/1992 | Vera |
| 5,160,315 A | 11/1992 | Heinecke |
| 5,176,703 A | 1/1993 | Peterson |
| 5,263,970 A | 11/1993 | Preller |
| 5,336,162 A | 8/1994 | Ota |
| 5,425,702 A | 6/1995 | Carn et al. |
| 5,531,855 A | 7/1996 | Heinecke et al. |
| 5,534,010 A * | 7/1996 | Peterson ............ 606/215 |
| 5,685,833 A | 11/1997 | Turngren |
| 5,733,251 A | 3/1998 | Johns |
| 5,733,570 A | 3/1998 | Chen |
| 5,738,642 A | 4/1998 | Heinecke et al. |
| 5,779,659 A | 7/1998 | Allen |
| 5,849,325 A | 12/1998 | Heinecke |
| 5,891,078 A | 4/1999 | Turngren |
| 5,979,450 A | 11/1999 | Baker et al. |
| 5,981,823 A | 11/1999 | Turngren |
| 6,129,971 A | 10/2000 | Brandt |
| 6,149,614 A | 11/2000 | Dunshee |
| 6,169,224 B1 | 1/2001 | Heinecke |
| 6,264,976 B1 | 7/2001 | Heinecke |
| 6,329,564 B1 | 12/2001 | Lebner |
| 6,364,188 B1 | 4/2002 | Dunshee |
| 6,420,622 B1 | 7/2002 | Johnston |
| 6,436,432 B2 | 8/2002 | Heinecke |
| 6,461,467 B2 | 10/2002 | Blatchford |
| 6,495,230 B1 | 12/2002 | do Canto |
| 6,548,727 B1 | 4/2003 | Swenson |
| 6,566,575 B1 | 5/2003 | Stickels |
| 6,596,917 B2 | 7/2003 | Oyaski |
| 6,607,799 B1 | 8/2003 | Heinecke |
| 6,822,133 B2 | 11/2004 | Lebner |
| 6,831,205 B2 | 12/2004 | Lebner |
| 6,982,359 B1 | 1/2006 | Beaudry |
| 2004/0106888 A1 * | 6/2004 | Lutri et al. ............ 602/54 |
| 2004/0204740 A1 | 10/2004 | Weiser |
| 2004/0243040 A1 | 12/2004 | Weiser |
| 2005/0182443 A1 * | 8/2005 | Jonn et al. ............ 606/213 |

FOREIGN PATENT DOCUMENTS

WO    WO2005/079674 A1    1/2005

OTHER PUBLICATIONS

Stalar: "A more effective way to wound closure," by S. Paris, Abstract, Pub. by 43 Intern'l Sci. and Eng. Fair, Nashville, Tennessee, May 10, 1992, p. 257.

Paris, Stacy: "Is there a more effective way to accomplish wound closure than those presently employed?"; author indicates abstract published by South Carolina Junior Academy.

* cited by examiner

WOUND CLOSURE KIT AND METHOD OF USING THE SAME

CROSS-REFERENCE TO RELATED APPLICATIONS

This application is a continuation-in-part of U.S. patent application. Ser. No. 11/200,423 filed on Aug. 9, 2005 and entitled "Four component wound closure device with locking strip".

BACKGROUND OF THE PRESENT INVENTION

1. Field of the Invention

The present invention relates generally to the field of medical devices and surgical instruments, and more specifically to the field of devices and systems for dressing and closing a laceration or incision.

2. History of the Related Art

Compositions and methods for laceration or incision closure are known in the art. The use of sutures or staples to close a laceration or incision represents the most common of these prior art techniques. The use of sutures or staples is an invasive technique that can be painful and frequently requires the use of an anesthetic. These procedures often leave unsightly scars, both from the secondary insertion holes as well as spacing and depth variations that result in varying tensions applied to the laceration or surgical incision between the suturing points and intervening spaces. Moreover, these skin closure techniques necessitate follow-up visits to a hospital or doctor's office for removal.

Alternative means for laceration closure have been previously disclosed, for example in U.S. Pat. No. 4,423,731 to Roomi, issued in 1984. The Roomi invention included a surgical dressing consisting of two strips of adhesive plaster placed in parallel about a wound edge. A series of filaments attached to each plaster strip, which are selectively attachable across the breadth of the wound to two additional plaster adhesive strips that were placed outside the former pair. Tension applied to the outer strips caused the inner strips to approach each other, thus placing pressure on the skin about the wound and effectively closing it.

While the Roomi invention was a step forward in the design of surgical dressings, it nevertheless contained several design problems. As pointed out in U.S. Pat. No. 5,534,010 to Peterson, the Roomi device needed improvement in two areas. First, according to Peterson, the Roomi device did not have a sufficient number of filaments and would better draw the wound together with more filaments: additionally a large number of threads would apply pressure against the wound similar to an adhesive pad which Peterson claims promotes healing. Secondly, the Peterson patent argues that the Roomi device is inefficient because it attaches the filaments to the side of the outside adhesive strips, as opposed to the end of the inner strips that would allegedly provide greater tension across the wound itself. In summary, the Peterson device is predicated in part upon the supposition that the Roomi device is improperly configured for high-tension applications, which are arguably necessary in areas of high vascular concentration.

Like the Roomi device, the Peterson invention includes a series of four flat tape strips that are joined together by interlaced filaments that span a wound to be closed. The Roomi & Peterson patents suffer from a number of serious deficiencies. The first deficiency is the failure to secure the two tape strips adjacent to the wound from lateral movement relative to each other once the device is closed. While the filaments may be effective at preventing the strips from parting outward they are not secure relative to each other along the wound edge. The Roomi patent requires long filaments as the attaching strips fall beyond the opposing pads. The Peterson patent while having shorter filaments teaches a series of filaments that do not attach to the respective tape strips at or near the wound site. Elementary geometry teaches us that the stability of any device of this type will depend highly on the length that the filaments must traverse between fixed points. Given the geometry of the Peterson device, it is evident that the length of the filaments combined with the distance that they must span between fixed points renders the device relatively unstable. In particular, any shearing or torque movement of the bandage components that are attached to the wound edges will decrease stability of the bandage during healing. Accordingly, the Peterson invention leaves the user open to certain risks including the movement of the bandage components relative to each other directly adjacent to the wound itself.

The Peterson and the Roomi devices present further risks by leaving the filaments or crossing members exposed to potential snags or pulling. Exposed filaments are particularly susceptible to pulling, snagging or tearing when in contact with clothing or the user's daily wear. The Peterson patent teaches that a specific deficiency of the Roomi device was that it does not have enough filaments to generate the necessary tension. Accordingly, the Peterson device specifically teaches using up to twenty-six filaments per linear inch. The added number of filaments required in the Peterson device compounds the problem by vastly increases the risk that the device itself will become snagged and could dislodged from the user. As the Peterson device is not particularly stable about the wound site, this increase in the number of filaments only exacerbates these risks.

Finally, Peterson teaches that a large number of filaments is necessary to generate the tension necessary for certain applications, but there is little in existing surgical publications that lend credence to this claim. However, as the density of the filaments increases according to Peterson's teachings, the strips near the wound edges become increasingly difficult to adjust relative to each other during application. This is a serious problem as the strips can never be applied perfectly relative to one another and always require some lateral adjustment. If there is not enough adjustability the wound could be closed in a bad position. Adjustability is feature that improves with fewer filaments (opposite Peterson's teaching). As such, the applications suitable for the Peterson device are rather limited in scope. The Peterson device does not present a solution to the principal problem of the Roomi device, e.g. the lack of security of the device when closed; but rather proposes solutions to issues that are unimportant and have simply engendered another set of problems outlined above.

Liquid bandages and other adhesive-type compositions have also been used widely in the medical arts. These types of closures are generally best suited for superficial or minor wounds, as skin adhesives do not draw the skin together or align the edges. It is difficult to align the skin edges and compress a larger or deeper wound manually or with the use of forceps, which is required to apply a liquid adhesive to the wound. In the case of liquid wound closure means, again that art is lacking in devices and methods that provide rigid dimensional stability in combination with precision alignment of the wound edge and maintenance of the healing process. Although these and other compositions and methods for closing wounds or incisions are known in the art, the aforementioned problems have prevented them from gaining popular acceptance. While there is a clear need for a minimally invasive composition or method for wound or incision closure that is practical and easy to use, such a composition or method must retain its dimensional stability after being secured in order to prevent any additional trauma to the wound while simultaneously being readily adjustable and adaptable for different wound closure applications.

SUMMARY OF THE PRESENT INVENTION

Accordingly, the present invention includes a wound closure device, a wound closure kit, and method of making and using the same that solves the problems noted above. In particular, the device of the present invention includes a first and a second interlaced component, each having an adhesive-backed wound edge pad for attachment to the skin of an individual adjacent a laceration or incision to be closed. In use, the adhesive-backed pad of the first interlaced component is applied along a first side of the wound or incision and the adhesive-backed pad of the second interlaced component is applied along a second side of the wound or incision.

Each of the wound edge pads is attached to an opposing tension adjusting pad that also has an adhesive backing. Providing tension to the tension pads during use translates the relative positions of the wound edge pads such that the wound itself is closed or substantially closed. The adhesive backing on the tension adjusting pads allows a user to securely deposit the tension adjusting pads on the individual's skin adjacent to and outboard of the opposing wound edge pad.

The wound edge pads are connected to the respective tension adjusting pads by elongate connecting elements that may be flat or tubular in shape. Moreover, the present invention includes embodiments in which the elongate connecting elements are integrated into the wound edge pads, and alternate embodiments in which the elongate connecting elements are attached or affixed to the noted components through conventional means. Also, the elongated connectors are sufficiently spaced to allow for lateral adjustment of the wound edge pads during application.

The present invention also includes various means for restraining or immobilizing the elongated connectors relative to the wound edge pads and adding dimensional stability and rigidity to the device. One such means includes one or more adhesive-backed locking strips for securing the elongate connecting elements as they span between the first interlaced component and the second interlaced component. The locking strips may be integrated into or separately attached to one or more of the wound edge pads, such that in use the locking strips effectively attach to the wound edge pads while immobilizing the elongate connecting elements there between. The locking strip essentially locks the filaments and holds the wound edge pads more securely in a fixed position reducing the movement of the pads on either side of the wound relative to each other. Also, the locking strip covers the filaments eliminating potential snags and breaks for a safer closure.

In the single locking strip embodiment, the locking strip includes a central region that is perforated or porous in nature thus providing access to the wound site for the application of medicaments and the transference of exudates away from the incision or laceration.

The present invention also relates to a substructure and a means for making the same that is adapted for use with the device. As described more fully below, the substructure may be composed of woven components that are further woven or non-woven, knitted, or otherwise connected together by crossing members. As such, the substructure is designed to include elongate connecting elements, i.e. crossing members; and by fitting or attaching the remaining components of the present invention thereto, the device disclosed herein can be readily manufactured with a continuous process to produce unlimited lengths.

The present invention also relates to an adhesive that can be applied to the device in a liquid form such that it penetrates the device prior to curing. Once the curing has occurred, the adhesive will add additional rigidity and strength to the device of the present invention and thus increase the dimensional stability and protective nature of the device. The adhesive may be contained within a container that is readily adapted for application of the adhesive in a liquid form to the device. The adhesive could optionally contain anti-microbial agents, occlude the wound site and serve as a barrier for infection.

These and further features and advantages of the present invention are more apparent from the following detailed description read with reference to the following Figures.

DETAILED DESCRIPTION OF THE PREFERRED EMBODIMENTS

The present invention includes a four-component wound closure device 10 that solves the aforementioned problems through the incorporation of novel elements into a unique design. In particular, the configuration of the device 10 renders it easy to apply and use, as well as providing for the comfort and safety of the individual to whom it is affixed. Moreover, in specific embodiments of the present invention discussed below, the device 10 provides access to the wound for the application of medicaments or the removal of exudates. For purposes of the specification, the term wound shall refer to those types of cuts, lacerations or surgical incisions that are commonly treatable through closing the surrounding tissue. The present invention may be readily manufactured through means disclosed herein as well as other means applicable to existing devices.

Figure 1:
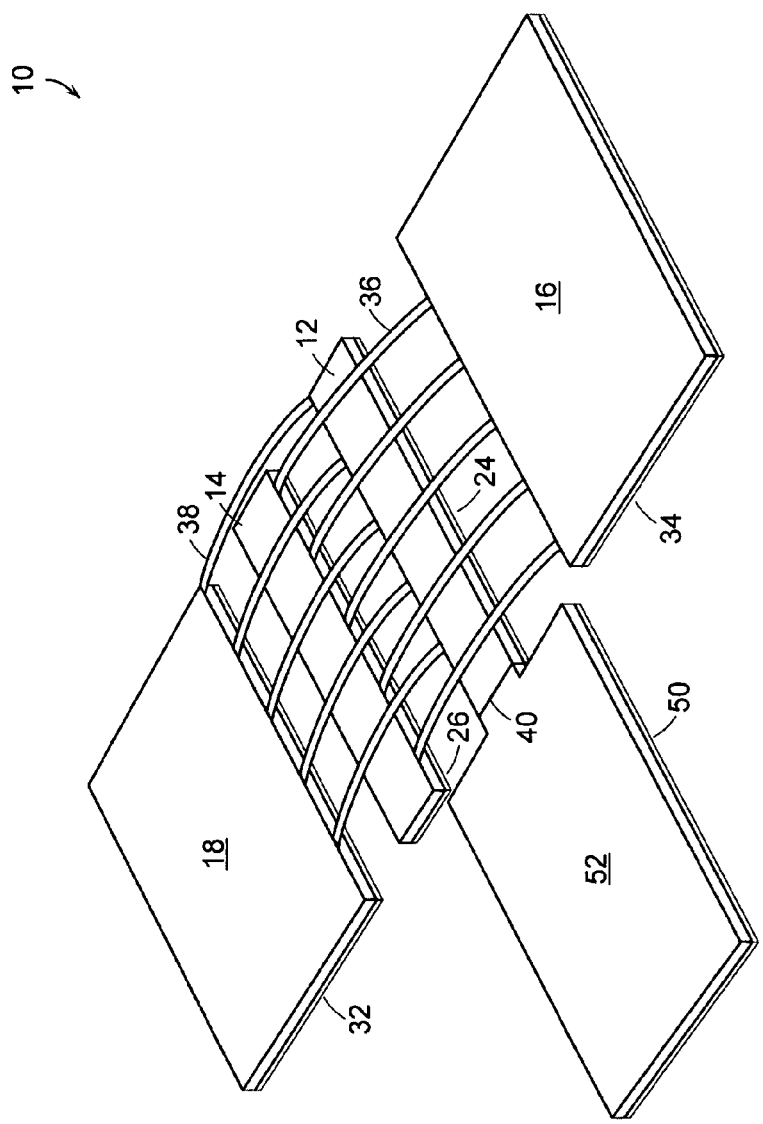
FIG. 1 is a perspective view of a four-component wound closure device in accordance with a preferred embodiment of the present invention.
Figure 2:
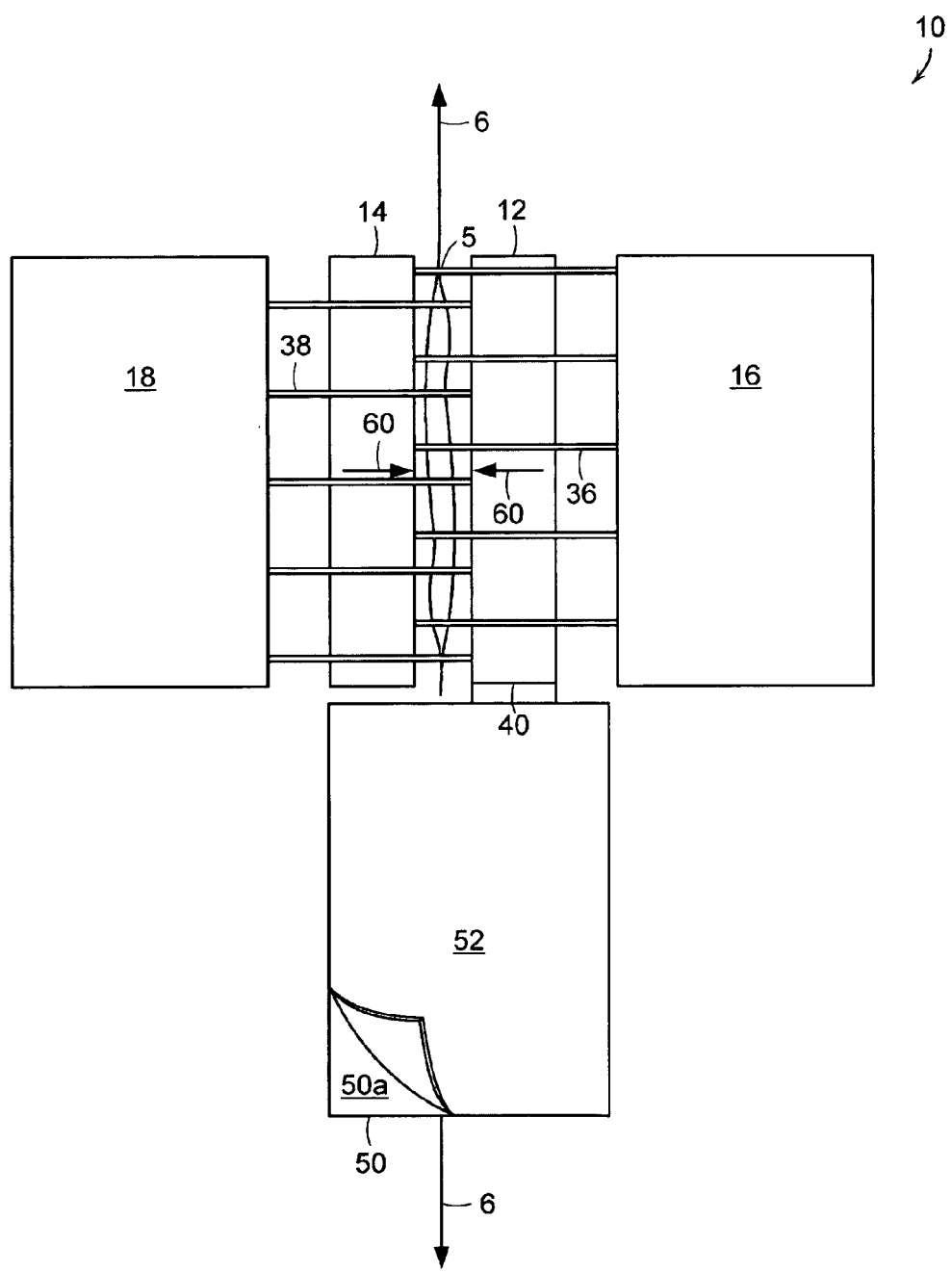
FIG. 2 is a plan view of the wound closure device illustrated in FIG. 1.

FIG. 1 is a perspective view of a four-component wound closure device 10 in accordance with another embodiment of the present invention, and FIG. 2 is a plan view of the same. The device 10 includes a first wound edge pad 12 and a second wound edge pad 14 that are preferably disposable on either side of a laceration or incision in an individual's skin. The wound edge pads 12, 14 can be comprised of a number of materials known in the art, although a clear and breathable material is preferable in order to permit observation of the wound site and surrounding skin throughout the healing process.

In preferred embodiments, the wound edge pads 12, 14 may be reinforced with a substantially rigid material, such as a rigid polymer, nylon, or additional layers of semi rigid polymeric materials in order to provide and maintain the dimensional stability of the device near the wound site during the healing process. Most preferably, the wound edge pads 12, 14 are reinforced along their interior edge, which is defined as the edge placed directly adjacent to the wound during use. Proper reinforcement of the wound edge pads 12, 14 is preferred in order to minimize any torsion or shearing forces that may dislodge the device 10 or traumatize the wound itself.

The wound edge pads 12, 14 are preferably coated with adhesive on one side, or alternatively each of the wound edge pads 12, 14 has an adhesive or glue disposed on its posterior surface (not visible in FIGS. 1 and 2). In order to maintain the adhesive before application, the first wound edge pad 12 has one or more release liners 24 selectively disposed there under; and the second wound edge pad 14 has one or more release liners 26 selectively disposed there under. As discussed further herein, the first and second release liners 24, 26 can be selectively removed in order to affix the wound edge pads 12, 14 about the edges of a wound.

The device 10 further includes a first tension adjusting pad 16 and a second tension adjusting pad 18 that are preferably comprised of a material similar or identical to that of the wound edge pads 12, 14. Like the wound edge pads 12, 14, the tension adjusting pads 16, 18 are preferably adhesive on or have an adhesive or glue disposed on their posterior surfaces (not visible in FIGS. 1 and 2). In order to prevent inadvertent adhesion, the first tension adjusting pad 16 has a third release liner 34 disposed on its posterior surface; and the second tension adjusting pad 18 has a fourth release liner 32 disposed on its posterior surface. As discussed further herein, the third and fourth release liners 34, 32 can be selectively removed in order to affix the tension adjusting pads 16, 18 to the individual's dermis adjacent to the respective wound edge pads 12, 14.

The device 10 further includes a plurality of elongate connecting elements 38 that connect the first wound edge pad 12 to the second tension adjusting pad 18; as well as a second plurality of elongate connecting elements 36 that connect the second wound edge pad 14 to the first tension adjusting pad 16. The elongate connecting elements 36, 38 can be produced from any flexible, non-elastic material that is securable to the wound edge pads 12, 14 and the tension adjusting pads 16, 18. The entire device can be rendered sterile. Examples of preferred materials for the elongate connecting elements 36, 38 include monofilament or multifilament polymers, extruded films or textiles. The elongate connecting elements 36, 38 may be secured to the wound edge pads 12, 14 and the tension adjusting pads 16, 18 in any conventional means, including for example stitching or adhesion. Alternatively, the elongate connecting elements 36, 38 may be woven, knitted or stitch bonded into a substructure that serves as the foundation for the wound edge pads 12, 14 and the tension adjusting pads 16, 18 construction.

The elongate connecting elements 36, 38 are preferably plural in numbers, such that the tension exerted on the wound edge pads 12, 14 by the tension adjusting pads 16, 18 is substantially uniform in the direction perpendicular to the elongate connecting elements 36, 38. While ten total elongate connecting elements 36, 38 are shown in FIG. 1, it should be understood that this is for illustrative purposes only, and the precise number of elongate connecting elements 36, 38 provided with the device 10 is a matter of engineering and design choice. Preferably, the elongate connecting elements 36, 38 are sufficient in length such that the tension adjusting pads 16, 18 can be affixed to the individual's skin at least 2 centimeters from the wound itself. More particularly, the elongate connecting elements 36, 38 are preferably between 2 and 5 centimeters in length thus providing a user access to the area between the affixed wound edge pads 12, 14 and tension adjusting pads 16, 18.

The device 10 preferably includes a single locking strip 50 that defines in part an anterior surface 50a. The anterior surface 50a is preferably adhesive in nature, such that it has an adhesive, glue or other adhesion means applied thereto for affixing the locking strip 50 to another surface. The locking strip 50 is preferably connected to or integral with one of the wound edge pads 12, 14. Alternatively, the locking strip 50 may be separate from the wound edge pads 12, 14 and applied thereto following alignment of the device 10. As depicted herein, the locking strip 50 is integrated with the first wound edge pad 12, but it should be understood that integration with the second wound edge pad 14 is equally preferred. A crease or division 40 serves as a marker for assisting a user in removing a fifth release liner 52 and folding and depositing the anterior surface 50a of the locking strip 50 to another surface.

The device 10 is best utilized for closing a wound 5 that is oriented along a longitudinal axis 6, shown in FIG. 2. In use, the device 10 is oriented such that the wound edge pads 12, 14 are deposited adjacent to the wound 5 such that the elongate connecting elements 36, 38 are substantially perpendicular to the longitudinal axis 6. In this manner, the elongate connecting elements 36, 38 serve to maximize the distribution of tension along the length of the wound edge pads 12, 14, which in turn creates a uniform pressure about the edges of the wound 5 in order to speed healing.

Figure 3:
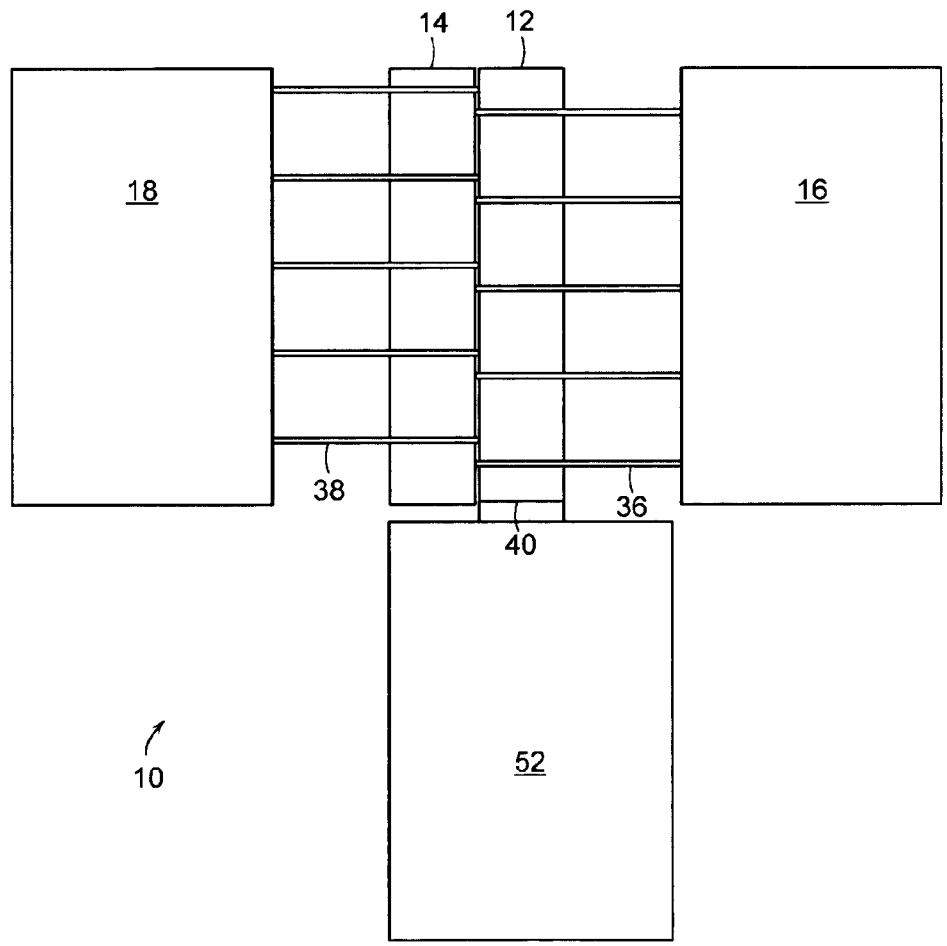
FIG. 3 is a plan view of the wound closure device in use as illustrated in FIG. 1.

Following removal of the first release liner 24 and the second release liner 26, the wound edge pads 12, 14 are affixed to the individual's skin, the tension adjusting pads 16, 18 are pulled in a direction substantially perpendicular to 6 longitudinal axis as shown in FIG. 3. Once the appropriate tension has been achieved, a user can remove the third release liner 34 and the fourth release liner 32 from the tension adjusting pads 16, 18 and affix the same to the individual's skin.

Figure 4:
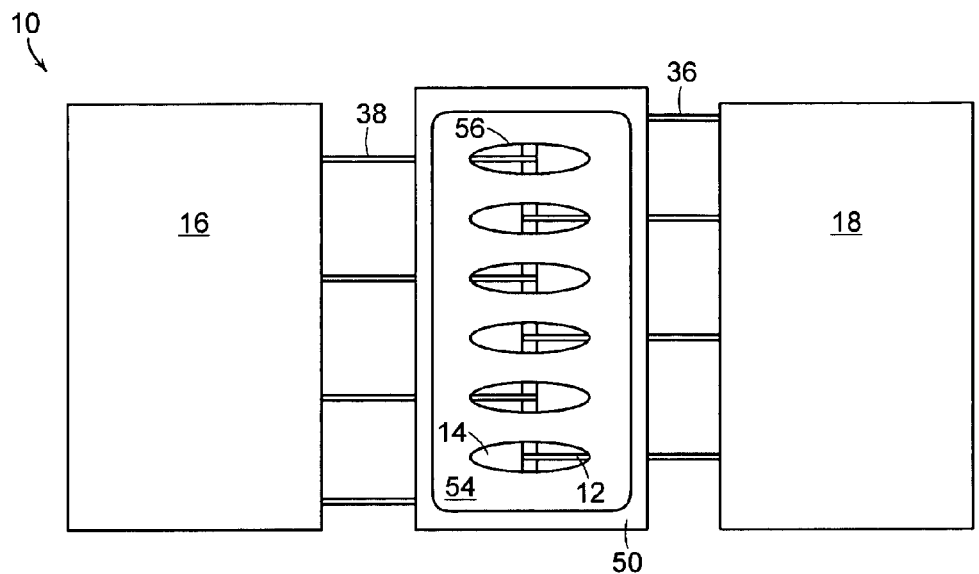
FIG. 4 is a plan view of the wound closure device in use as illustrated in FIG. 1 including additional features.

FIG. 4 is a plan view of the device 100 in use following removal of the fifth release liner 52. As shown herein, the locking strip 50 is folded or otherwise placed such that its anterior surface 50a is directly adjacent to the wound edge pads 12, 14 with the elongate connecting elements 36, 38 immobilized there between. If the locking strip 50 is not integrated into the wound edge pads 12, 14, then it can be simply placed over the former by a user in a manner known in the art. The single locking strip 50 totally covers the wound edge pads 12, 14 as well as the wound 5 itself.

In order to ensure proper access to the wound 5 for treatment purposes, the locking strip 50 preferably includes a central region 54 that is porous or otherwise semi permeable in nature. For example, the central region 54 can be comprised of an open textile structure such as a gauze or non-woven pad to permit the flow of exudates away from the wound site also to provide access for the application of topical medicaments. Alternatively, the central region can be comprised of materials identical to the locking strip 50 but having perforations or cutouts formed therein. In a preferred embodiment, the central region 54 defines one or more apertures or openings 56 through which a user can treat the wound 5 while the device 10 is in use. In particular, the one or more openings 56 allow for the easy application of medicaments and permit the easy removal of wound exudates while the device 10 maintains the proper tension and pressure needed to close the wound 5.

Figure 5:
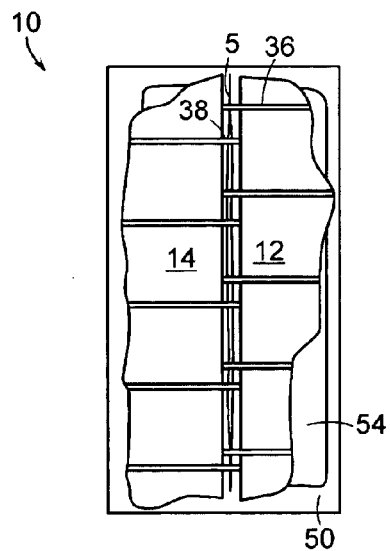
FIG. 5 is a cutaway plan view of the wound closure device in use as illustrated in FIG. 1.

After securing the locking strip 50 to the wound edge pads 12, 14, the exposed elongate connecting elements 36, 38 can be removed along with the tension adjusting pads 16, 18. Alternatively, if the user so desires the device 10 in its entirety can be left in place for enhanced dimensional stability depending on the patient's anatomy. As shown in the partial cutaway plan view of FIG. 5, the device 10 effectively covers and closes the wound 5 through the placement of the wound edge pads 12, 14 and the locking strip 50. As the elongate connecting elements 36, 38 are removed in this stage of healing, there is a minimal risk that any torsion or shearing force will affect the wound edge pads 12, 14 and aggravate the wound 5. Moreover, as the locking strip 50 preferably contains the central region 54, preferably defining one or more openings 56 as described above, the device 10 of the present invention assures that a user will have access to the wound 5 for treatment purposes.

Figure 6:
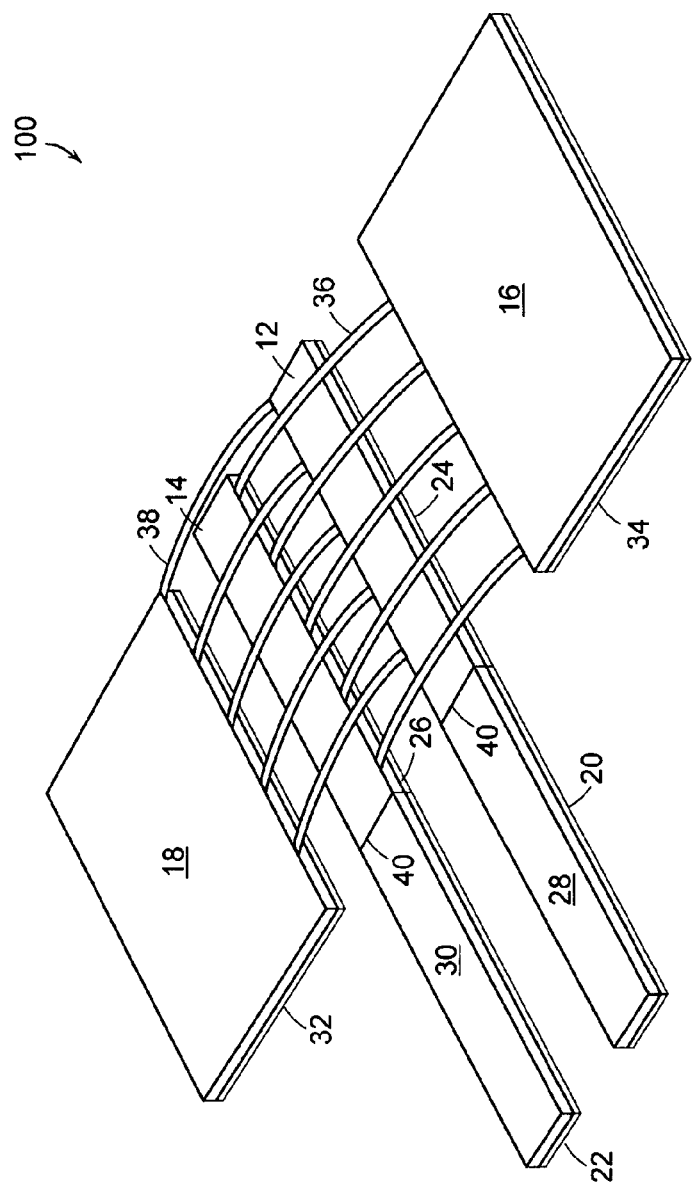
FIG. 6 is a perspective view of a four-component wound closure device in accordance with another embodiment of the present invention.
Figure 7:
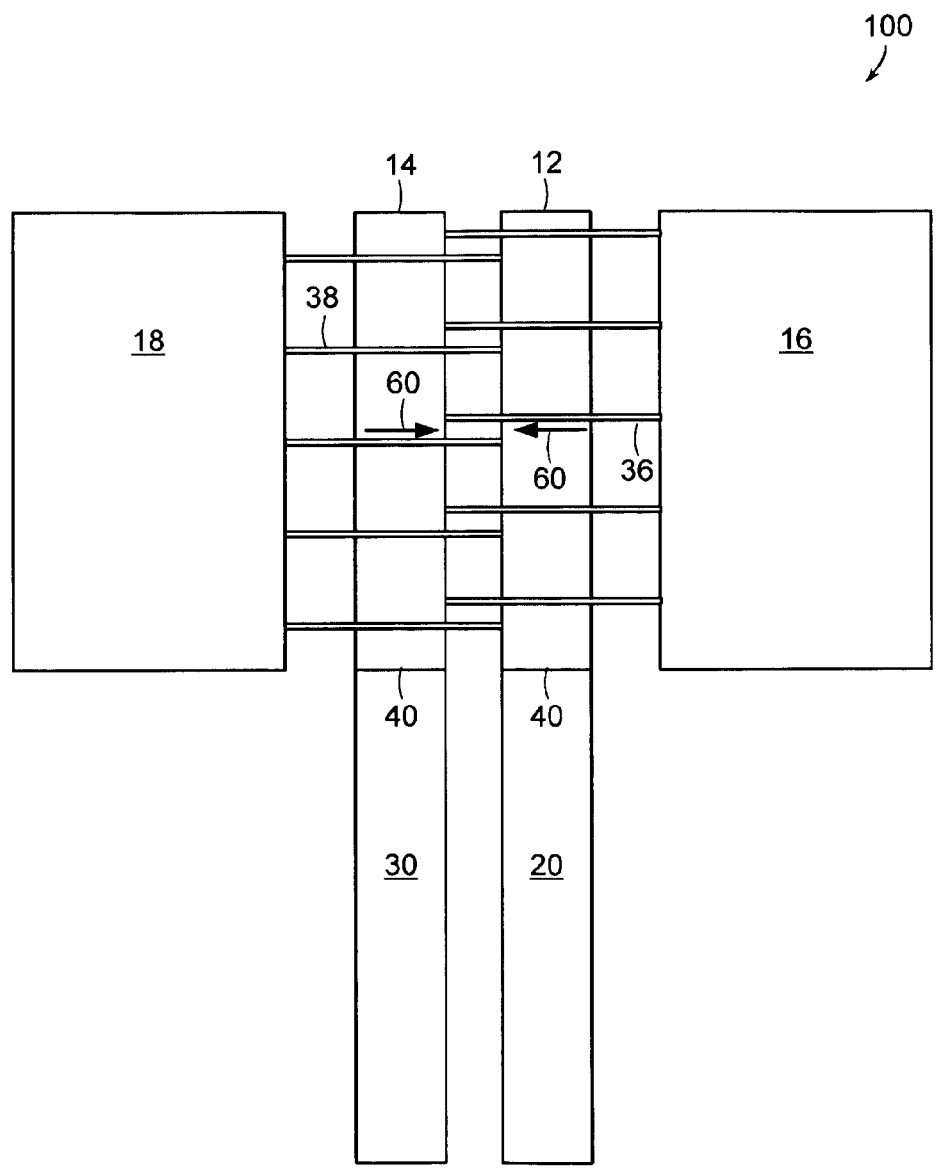
FIG. 7 is a plan view of the wound closure device illustrated in FIG. 6.

FIG. 6 is a perspective view of a device 100 in accordance with another embodiment of the present invention, and FIG. 7 is a plan view of the same. As in the previous embodiment, the device 100 includes a first wound edge pad 12 and a second wound edge pad 14 that are preferably disposable on either side of a laceration or incision in an individual's skin. The wound edge pads 12, 14 can be comprised of a number of materials known in the art, although a clear and breathable material is preferable in order to optimize observation and treatment of the wound itself.

As in the prior embodiment, the wound edge pads 12, 14 are optionally reinforced with a substantially rigid material, such as a rigid polymer, nylon, or additional layers of semi rigid polymeric material in order to provide support and maintain the dimensional stability of the device 100 throughout the entire healing process. Most preferably, the wound edge pads 12, 14 are reinforced along their interior edge, which is defined as the edge placed directly adjacent to the wound during use. Reinforcement of the wound edge pads 12, 14 is preferred in order to minimize any torsion or shearing forces that may dislodge the device 100 or traumatize the wound itself.

The wound edge pads 12, 14 are preferably adhesive on one side, or alternatively each of the wound edge pads 12, 14 has an adhesive or glue disposed on its posterior surface (not visible in FIGS. 6 and 7). The first wound edge pad 12 has a first release liner 24 selectively disposed there under; and the second wound edge pad 14 has a second release liner 26 selectively disposed there under. As described in the prior embodiment, the first and second release liners 24, 26 can be selectively removed in order to affix the wound edge pads 12, 14 about the edges of a wound.

The device 100 further includes a first tension adjusting pad 16 and a second tension adjusting pad 18 that are preferably comprised of a material similar or identical to that of the wound edge pads 12, 14. Like the wound edge pads 12, 14, the tension adjusting pads 16, 18 are preferably adhesive on or have an adhesive or glue disposed on their posterior surfaces (not visible in FIGS. 6 and 7). In order to prevent inadvertent adhesion, the first tension adjusting pad 16 has a third release liner 34 disposed on its posterior surface; and the second tension adjusting pad 18 has a fourth release liner 32 disposed on its posterior surface. As discussed further herein, the third and fourth release liners 34, 32 can be selectively removed in order to affix the tension adjusting pads 16, 18 to the individual's dermis adjacent to the respective wound edge pads 12, 14.

The device 100 further includes a plurality of elongate connecting elements 38 that connect the first wound edge pad 12 to the second tension adjusting pad 18; as well as a second plurality of elongate connecting elements 36 that connect the second wound edge pad 14 to the first tension adjusting pad 16. The elongate connecting elements 36, 38 can be produced from any flexible, non-elastic material that is securable to the wound edge pads 12, 14 and the tension adjusting pads 16, 18 and can be rendered sterile. Examples of preferred materials for the elongate connecting elements 36, 38 include polymeric monofilaments or multifilament polymers/polymeric structures, extruded films or textiles, any of which may contain textile fibers. The elongate connecting elements 36, 38 may be secured to the wound edge pads 12, 14 and the tension adjusting pads 16, 18 in any conventional means, including for example stitching or adhesion. Alternatively, the elongate connecting elements 36, 38 may be woven, knitted or stitch bonded into a substructure that serves as the foundation for the wound edge pads 12, 14 and the tension adjusting pads 16, 18 construction.

The elongate connecting elements 36, 38 are preferably plural in numbers, such that the tension exerted on the wound edge pads 12, 14 by the tension adjusting pads 16, 18 is substantially uniform in the direction perpendicular to the elongate connecting elements 36, 38. While ten total elongate connecting elements 36, 38 are shown in FIG. 6, it should be understood that this is for illustrative purposes only, and the precise number of elongate connecting elements 36, 38 provided with the device 100 is a matter of engineering and design choice.

As noted above, the elongate connecting elements 36, 38 are sufficient in length such that the tension adjusting pads 16, 18 can be affixed to the individual's skin at least 2 centimeters from the wound itself. More particularly, the elongate connecting elements 36, 38 are preferably between 2 and 5 centimeters in length thus providing a user access to the area between the affixed wound edge pads 12, 14 and tension adjusting pads 16, 18.

The present embodiment further includes a first locking strip 20 and a second locking strip 22 that are selectively disposable on the elongate connecting elements 36, 38. More particularly, in the embodiment depicted in FIG. 6, the first and second locking strips 20, 22 are selectively disposable on the anterior surfaces of the first and second wound edge pads 12, 14, respectively, with the elongate connecting elements 36, 38 disposed there between. The locking strips 20, 22 preferably are adhesive coated on their anterior surfaces (not visible in FIGS. 6 and 7), which are selectively covered by a sixth release liner 28 and a seventh release liner 30 respectively.

In one embodiment shown in FIG. 6, the first locking strip 20 is preferably attached to or integral with the first wound edge pad 12. Similarly, the second locking strip 22 is preferably attached to or integral with the second wound edge pad 14. Disposed between each respective component is a crease or division 40 about which the locking strips 20, 22 are foldable relative to the wound edge pads 12, 14. Alternatively, the first locking strip 20 and the second locking strip 22 may be separate from the respective wound edge pads 12, 14, such that the former are discrete elements of the device 10 that are applied during use in a manner familiar to those skilled in the art. Accordingly, as described more fully below, upon removal of the sixth and seventh release liners 28, 30, the locking strips 20, 22 can be selectively folded and attached to the wound edge pads 12, 14 thus securing the elongate connecting elements 36, 38 there between.

Figure 8:
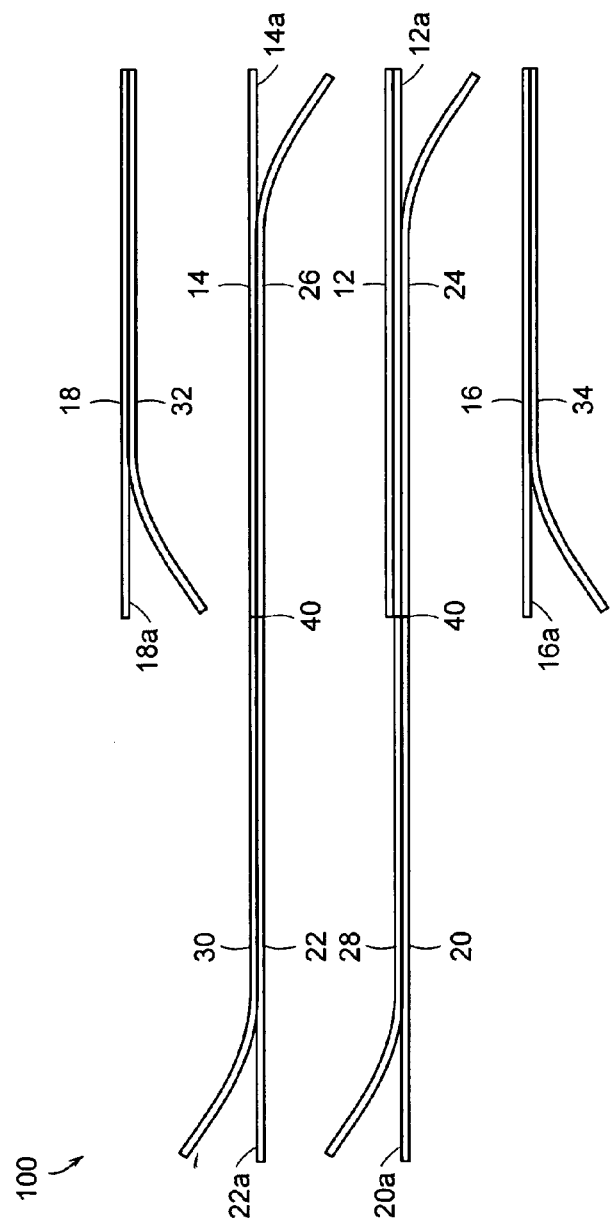
FIG. 8 is a partial cross-sectional view of the wound closure device illustrated in FIG. 6.

FIG. 8 is a partial cross-sectional view of the device 100 illustrated in FIG. 6, with the elongated connecting elements 36, 38 removed for clarity. As shown in FIG. 8, in one embodiment of the present invention each of the components consists of a primary layer with a release liner as described above. For example, the first wound edge pad 12 defines a posterior surface 12a, which as described above is adapted to adhere to a person's skin. The posterior surface 12a is further selectively covered by the first release liner 24, such that prior to use, the device 10 of the present invention is properly maintained. Similarly, the second wound edge pad 14 defines a posterior surface 14a having adhesive properties, which is selectively covered by the second release liner 26.

The first locking strip 20 defines an anterior surface 20a that is selectively covered by a sixth release liner 28; and the second locking strip 22 defines an anterior surface 22a that is selectively covered by a seventh release liner 30. As shown in FIG. 8, the first locking strip 20 is integrated into the first wound edge pad 12 while the second locking strip 22 is integrated into the second wound edge pad 14. While this configuration between the locking strips 20, 22 and the wound edge pads 12, 14 is preferred for this device 100, it should be understood that other configurations are equally suitable provided that the locking strips 20, 22 are selectively attachable to the respective wound edge pads 12, 14. For example, the locking strips 20, 22 may be discrete components that are not integrated into the device 10, but rather applied during use as described herein.

Each of the tension adjusting pads 16, 18 defines a posterior surface 16a, 18a, respectively, that also has adhesive properties. As described above, the third release liner 34 selectively covers the posterior surface 18a of the second tension adjusting pad 18, while the fourth release liner 32 covers the posterior surface 16a of the first tension adjusting pad 16. As in the case of the wound edge pads 12, 14, the tension adjusting pads 16, 18 are selectively covered by the release liners 34, 32 until such a time as the user is ready to apply the device 100 to the individual's skin.

Figure 9:
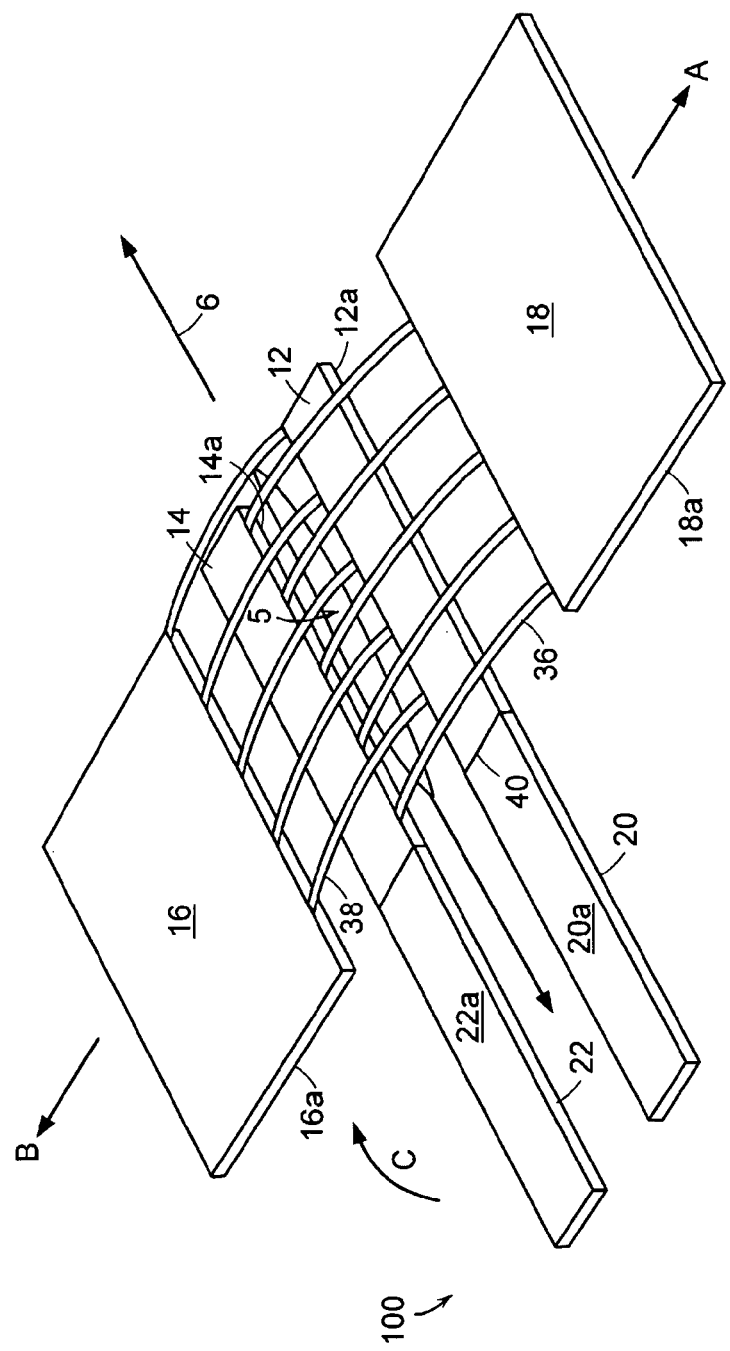
FIG. 9 is a perspective view of the wound closure device in use as illustrated in FIG. 6.

FIG. 9 is a perspective view of the device 100 in use about a typical wound 5. As illustrated herein, the release liners 24, 26, 28, 30, 32, 34 have been removed from their respective components, such that all the relevant surfaces are exposed. For example, posterior surfaces 12a, 14a, 16a, 18a and anterior surfaces 20a, 22a are exposed such that the adhesive properties of the device 100 can be utilized.

Figure 10:
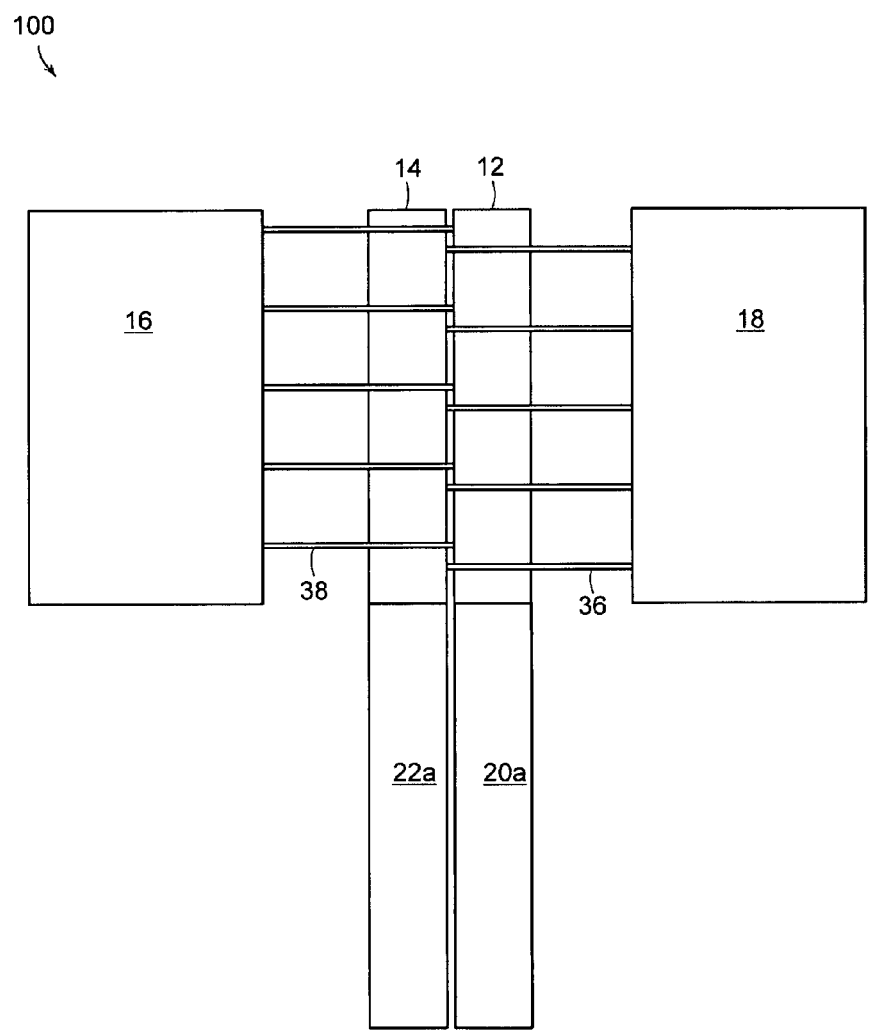
FIG. 10 is a plan view of the wound closure device in use as illustrated in FIG. 6.

In use, wound edge pads 12, 14 are placed adjacent to the wound 5 and substantially parallel with a longitudinal axis 6 of the wound 5. Once the adhesive of posterior surfaces 12a, 14a is sufficiently affixed to the individual's skin, the tension adjusting pads 16, 18 are pulled in a generally opposite directions that are generally perpendicular to the longitudinal axis 6. For example, first tension adjusting pad 16 is pulled in a direction along arrow B, while second tension adjusting pad 18 is pulled in a direction along arrow A. As previously noted, the elongated connecting elements 36, 38 distribute the applied tension to the wound edge pads 12, 14 which being affixed to the skin of the individual, function to close or substantially close the wound 5. Upon satisfactorily closing the wound 5, the tension adjusting pads 16, 18 can be affixed to the individual's skin, as shown in the plan view of FIG. 10.

Figure 11:
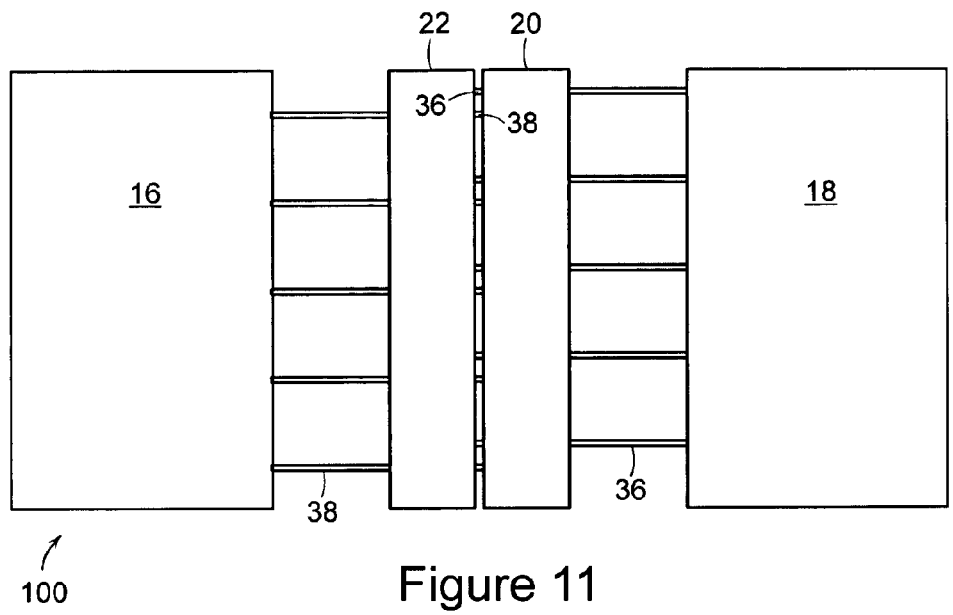
FIG. 11 is a plan view of the wound closure device in further use as illustrated in FIG. 6.

Following attachment of the tension adjusting pads 16, 18 to the individual's skin, the locking strips 20, 22 can be pivoted along arrow C such that anterior surfaces 20a, 22a will contact the respective wound edge pads 12, 14 as shown in FIG. 9. The resultant position of the locking strips 20, 22 is illustrated in FIG. 11. The locking strips 20, 22 adhere to the wound edge pads 12, 14 and immobilize the elongate connecting elements 36, 38 there under. As such, the device shown in FIG. 11 is contained about the wound 5 (not visible), and the elongate connecting elements 36, 38 are protected from interference, stretching or pulling. Moreover, the addition of the locking strips 20, 22 effectively limits any torsion or shearing forces that may dislodge the wound edge pads 12, 14 or the elongate connecting elements 36, 38.

Figure 12:
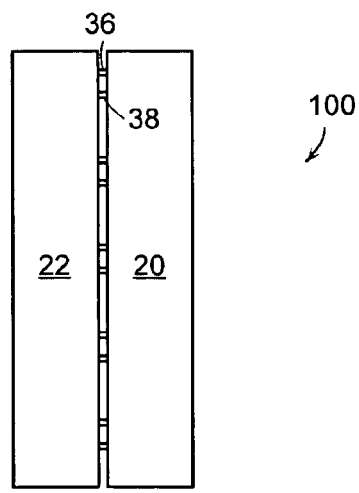
FIG. 12 is a plan view of the completely applied wound closure device in use as illustrated in FIG. 6.
Figure 13A:
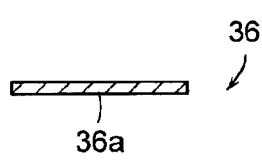
FIG. 13 is a cross-sectional representation of selected embodiments of an elongate connecting element in accordance with preferred embodiments of the present invention.
Figure 13B:
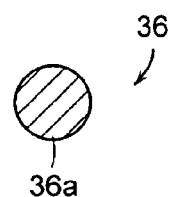
Figure 13C:
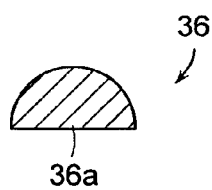
Figure 13D:
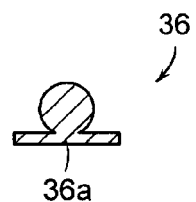

Once the locking pads 12, 14 have been sufficiently engaged to the wound edge pads 12, 14, the exposed elongate connecting elements 36, 38 and the tension adjusting pads 16, 18 attached thereto can be removed, as shown in FIG. 12. Removal of the tension adjusting pads 16, 18 can be affected by cutting or severing the exposed portions of the elongate connecting elements 36, 38; and the tension adjusting pads 16, 18 can be manually removed from the individual's skin. Accordingly, in the state depicted in FIG. 12, the present invention is secured about the wound 5 (not visible) and the risk of further trauma to the wound is minimized through removal of any extraneous components.

In one embodiment the device 10, 100 is preferably composed of a clear, breathable, polymeric material, such as for example polyurethane. In this embodiment, the wound edge pads 12, 14, tension adjusting pads 16, 18, the one or more locking strips 22, 24, 50, and the elongate connecting elements 36, 38 are composed of a polymeric material assembled in sheet form, such as extruded polyurethane sheets. In this embodiment, the elongate connecting elements 36, 38 are flat or ribbon-like in dimension, and attached to or otherwise integrated with the respective wound edge pads 12, 14 and tension adjusting pads 16, 18. Preferably, the components of the device 10, 100 are composed of a substantially inelastic stock so as to increase the rigidity of the device 10, 100. Alternatively, the wound edge pads 12, 14 and the tension adjusting pads 16, 18 can be reinforced with a substantially inelastic stock to increase their rigidity in selected locations, such as for example on edges nearest the site of the wound 5. In order to facilitate removal of the exposed elongate connecting elements 36, 38 and the tension adjusting pads 16, 18, it is preferred that the former components are perforated or otherwise mechanically biased for easy, manual removal.

Methods of manufacture for the device 10, 100 as set of interlocking polymers are known in the art and generally include the production of polymeric sheets of materials that are die cut to form specific shapes. These die-cut pieces define the wound edge pads 12, 14, tension adjusting pads 16 18 and elongate connecting elements 36, 38 of the device 10, 100 which are then interlaced through means known in the art. Suitable connecting means include the use of stitching, adhesives, and sonic welding for example.

Polymer extrusion permits a manufacturer to cast or create polymers in virtually any shape. Accordingly, in one embodiment of the device 10, 100 the elongate connecting elements 36, 38 are extruded such so as to maximize the surface area of the elongate connecting elements 36, 38 that will contact the wound edge pads 12, 14 thus further stabilizing the present invention in use.

In preferred embodiments of the present invention, the wound edge pads 12, 14 are adapted to evert (or raise) skin edges to promote wound healing. It is known in the art that everting, raising or mounding of the skin edges at the wound or incision site prevents wound inversion. One way in which this may be accomplished is to provide a bend at the wound edge pad 12, 14 at least along the edge that is directly adjacent to the wound 5 itself. The bend may be angled or arcuate. When attached to the skin this eversion edge tends to lift the edges of the skin at the point of closure contact, thereby promoting healing.

In further preferred embodiments, the device 10, 100 of the present invention is also adapted for wound closure alignment. Spacing between adjacent elongated connecting elements 36, 38, as discussed above, is relevant to the issue of wound closure alignment. Additionally, preferred embodiments of the bandage of the present invention include wound closure alignment indicators 60 (shown in FIGS. 2 and 7). These alignment indicators 60 are visual indicators that appear on the wound edge pads 12, 14 near the wound edge. Typically, they will appear as a line or an arrow generally perpendicular to the wound 5 or incision. In closing a wound or incision, a clinician typically closes the wound manually with his/her fingers at the approximate mid-point, and then makes a small mark or line perpendicular to the wound with a surgical pencil. These marks are used to align the device precisely with the wound alignment indicators 60 on the device 10, 100 of the present invention.

The device 10, 100 of the present invention can be optionally adapted for transdermal drug delivery. As is known in the art, a drug is deliverable transdermally through the skin. For such an application, a drug-containing patch is secured to at least one of the flat flexible components in such a way that the drug can be delivered through the skin. Given the fact that there will be no adhesive contact between the skin and the wound edge pads 12, 14 in the area of the drug delivery patch, it may be necessary to increase the size of the wound edge pads 12, 14 to secure the device 10, 100 in such a transdermal drug delivery embodiment. Transdermal drug delivery is well known in the art and a review of the background is not necessary to enable one of skill in the art to make and use the present invention.

The device 10, 100 of the present invention may optionally include an elastic tension indicator element (not shown). The purpose of the tension indicator element is to provide a visual indication that a desired tension has been reached while applying the bandage. For example, materials are known in the art which change color when a predetermined tension is applied. Similarly, other graphic representations may be used for this purpose. For example, a rectangular graphic representation may be applied to an elastic tension indicator element. As this tension indicator is stretched, the graphic representation of the rectangle stretches. This element may be designed such that the desired tension is indicated when the original rectangular representation is stretched to the point where it closely approximates a geometric square.

FIG. 13 is a cross-sectional profile of an elongate connecting element 36, shown in various embodiments denoted A, B, C and D. In each configuration shown, the elongate connecting element 36 defines a posterior surface 36*a* that is intended for interfacing with and contacting the wound edge pads 12, 14. While a number of embodiments for the elongate connecting element 36 are shown, it should be understood that a preferred embodiment should be selected based upon an intended application, and the following descriptions are merely exemplary of the scope of the device 10, 100 of the present invention.

In embodiment A, the elongate connecting element 36 is shown in a ribbon-like configuration having a rectangular cross-section. As shown, this design provides for a substantial posterior surface 36*a* for securing the device 10, 100. In embodiment B, the elongate connecting element 36 is thread-like or cylindrical in nature, defining a circular cross-section. This design provides for a less substantial posterior surface 36*a* comparatively speaking. Embodiment C shows the elongate connecting element 36 configured as a semi-cylinder defining a semicircular cross-section. While maintaining the benefits of a thread-like member, this design of the elongate connecting element 36 provides for a substantial posterior surface 36*a* for contacting the wound edge pads 12, 14. Embodiment D shows an extruded elongate connecting element 36 that has the geometrical properties of both the ribbon-like and the thread-like embodiments noted above. It provides a substantial posterior surface 36*a* like embodiment A while simultaneously providing the flexibility and tensile strength of a thread or tube as in embodiment B. While the elongate connecting element 36 of embodiment D may be extruded as a unitary piece, an alternative construction combining the respective elongate connecting elements 36 of embodiments A and B into a single unit is also preferred.

In an alternate embodiment, the wound edge pads 12, 14, tension adjusting pads 16, 18, and one or more locking strips 22, 24, 50 from polymeric materials assembled in sheet form consistent with the methods described above. As noted, extruded polyurethane is one preferred polymer that is well suited for these components and this method of manufacture. The elongate connecting elements 36, 38 are composed of a monofilament or multifilament material, such as an extruded polymer formed into thin strands or threads. Polyurethane, polyester and other synthetic materials known in the art are suitable for constructing the elongate connecting elements 36, 38. During assembly of the device 10, 100, the elongate connecting elements 36, 38 are then attached to the respective wound edge pads 12, 14 and tension adjusting pads 16, 18 in order to form the interleaved structure of the present invention. Conventional means for attaching, such as adhesive, glue, stitching, sonic welding and other mating processes known in the art are suitable for this purpose.

Figure 14:
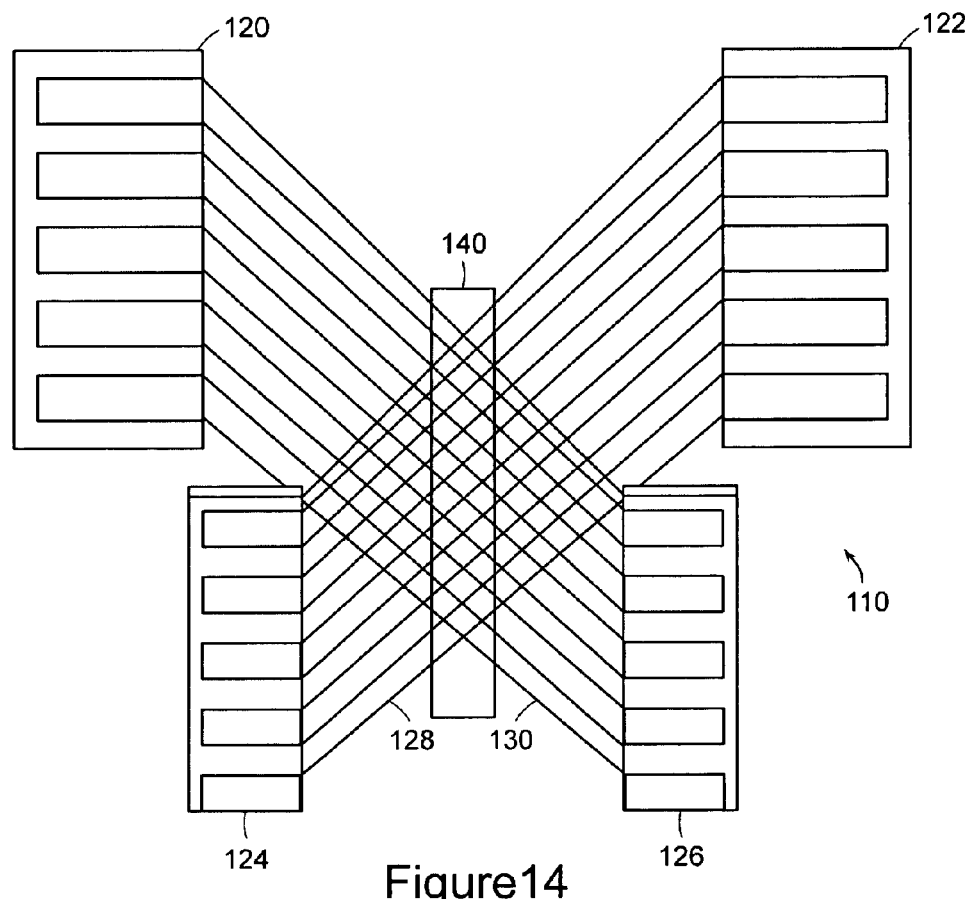
FIG. 14 is a schematic view of a substructure usable in the various embodiments of the present invention.

The device 10, 100 of the present invention can further include a substructure 110, illustrated in FIG. 14. The substructure 110 includes a first portion 120, a second portion 122, a third portion 124 and a fourth portion 126. The substructure 110 further includes a first connector 128 and a second connector 130. Each of the portions 120, 122, 124, 126 are preferably composed of a woven or knitted material, such as a textile material or a polymeric monofilament material, or some combination of each. The connectors 128, 130 are preferably composed of a textile material or a polymeric monofilament material, and may be strand-like or ribbon-like in configuration. For example, the connectors 128, 130 may be monofilament strands, textile ribbons, or extruded sheet polymer, depending upon the desired dimensions, rigidity and tensile strength as discussed in detail above.

The portions 120, 122, 124, 126 are preferably composed of identical materials that defined pores therein for receiving the connectors 128, 130 in a weaving, knitting or non-woven process. As shown in FIG. 14, the first connector 128 is woven, knitted or otherwise attached to both the second portion 122 and the third portion 124. In preferred embodiments, the first connector 128 is selectively woven or knitted into the second portion 122 and the third portion 124 thereby defining a homogenous structure. Similarly, the second connector 130 is woven, knitted or otherwise attached to both the first portion 120 and the fourth portion 126. In preferred embodiments, the second connector 130 is selectively woven or knitted into the first portion 120 and the fourth portion 126 thereby defining a homogenous structure.

Figure 15:
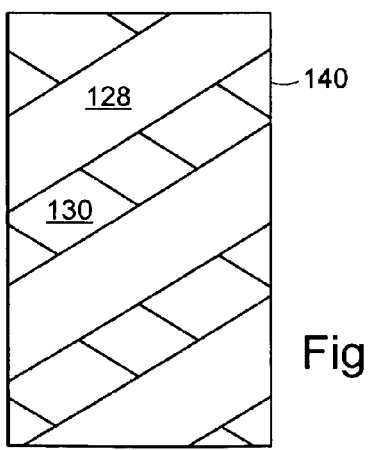
FIG. 15 is a magnified view of a portion of the substructure shown in FIG. 13.

In accordance with the present invention, the portions 120, 122, 124, 126 are interconnected by the connectors 128, 130 so as to define the interlaced substructure 110 shown in FIG. 14. The substructure 110 is manufactured in such a manner that the connectors 128, 130 are overlapping, thus prohibiting a user from pulling the device 10, 100 apart during application and use. The interlocking nature of the substructure is best seen in FIG. 15, which is a magnified view of a junction 140 where the first connector 128 and the second connector 130 cross.

The interlacing of the connectors 128, 130 can be accomplished through manual or automated means. In particular, the connectors 128, 130 can be manually stitched, woven, knitted or otherwise attached to their respective portions. Alternatively, the present invention includes a novel process for the automated fabrication of the substructure 110, described below.

In one preferred method, the substructure 110 is fabricated through a process of intermittent knitting, in which the connectors 128, 130 are automatically interlaced. For example, the first connector 128 is first woven or knitted into the third portion 124, and thereafter directed at the second portion 122 by a first knitting means. Likewise, the second connector 130 is first woven or knitted into the first portion 120, and thereafter directed at the fourth portion 126 by a second knitting means. During the knitting process, the first knitting means ceases for an interval of time, permitting the second knitting means to proceed to the fourth portion 126. After the interval of time, the first knitting means resumes its passage to the second portion 122, effectively disposing the first connector 128 over or on top of the second connector 130. After the juncture, each of the respective knitting means proceeds to weave or knit the connectors 128, 130 into the second portion 122 and the fourth portion 126, respectively.

A second passage is performed by the knitting means in which the first connector 128 returns from the second portion 122 to the third portion 124 and the second connector 130 returns from the fourth portion 126 to the first portion 120. As described previously, the first knitting means ceases for an interval of time, letting the second knitting means pass and place the second connector 130. Following the interval of time, the first knitting means resumes and places the first connector 128 over or on top of the second connector 130. After this second juncture, each of the respective knitting means proceeds to weave or knit the connectors 128, 130 into the third portion 124 and the first portion 120, respectively.

Given the foregoing description, it is clear that the intermittent knitting method can be extended indefinitely through any number of passes between the portions 120, 122, 124, 126. In preferred embodiments, the portions 120, 122, 124, 126 are indefinitely long such that the method described can produce continuous undetermined lengths. In such a manner, a substructure 110 of indeterminate length can be simply and automatically manufactured and later segmented, cut, or otherwise separated into sized substructures 110 usable with the device 10, 100 of the present invention.

In particular, the substructure 110 is readily adaptable for use with the device 10, 100 of the present invention, as the connectors 128, 130 are the functional analogs of the elongated connecting elements 36, 38 described in detail below. Similarly, it is contemplated that the first portion 120 and the second portion 122 will provide structural and dimensional support for the tension adjusting pads 16, 18, while the third portion 124 and the fourth portion 126 provide the same for the wound edge pads 12, 14.

The device 10, 100 can be manufactured with the substructure 110 of the present invention by augmenting the substructure 110 with the various components of the device 10, 100 presented above.

As described herein, the present invention includes a novel and inventive device for non-invasive wound closure and a method of making the same. In its particular embodiments, the device of the present invention includes at least one locking strip that is selectively adhered to the wound edge pads for securing the device and immobilizing the elongate connecting elements. Moreover, a substructure and method of making the same can be readily incorporated into the device of the present invention for increasing the rigidity and stability of the device while further automating and minimizing the costs of assembly.

The present invention further includes a four-component wound closure kit 200 that solves the aforementioned problems through the incorporation of novel elements into a unique design. In particular, the configuration of the kit 200 renders it easy to apply and use, as well as providing for the comfort and safety of the individual to whom it is affixed. As in the rest of the specification, the term wound shall refer to those types of cuts, abrasions, lacerations or incisions that are commonly treatable through closing the surrounding tissue. The present invention may be readily used through means disclosed herein as well as other means applicable to existing kits.

Figure 16:
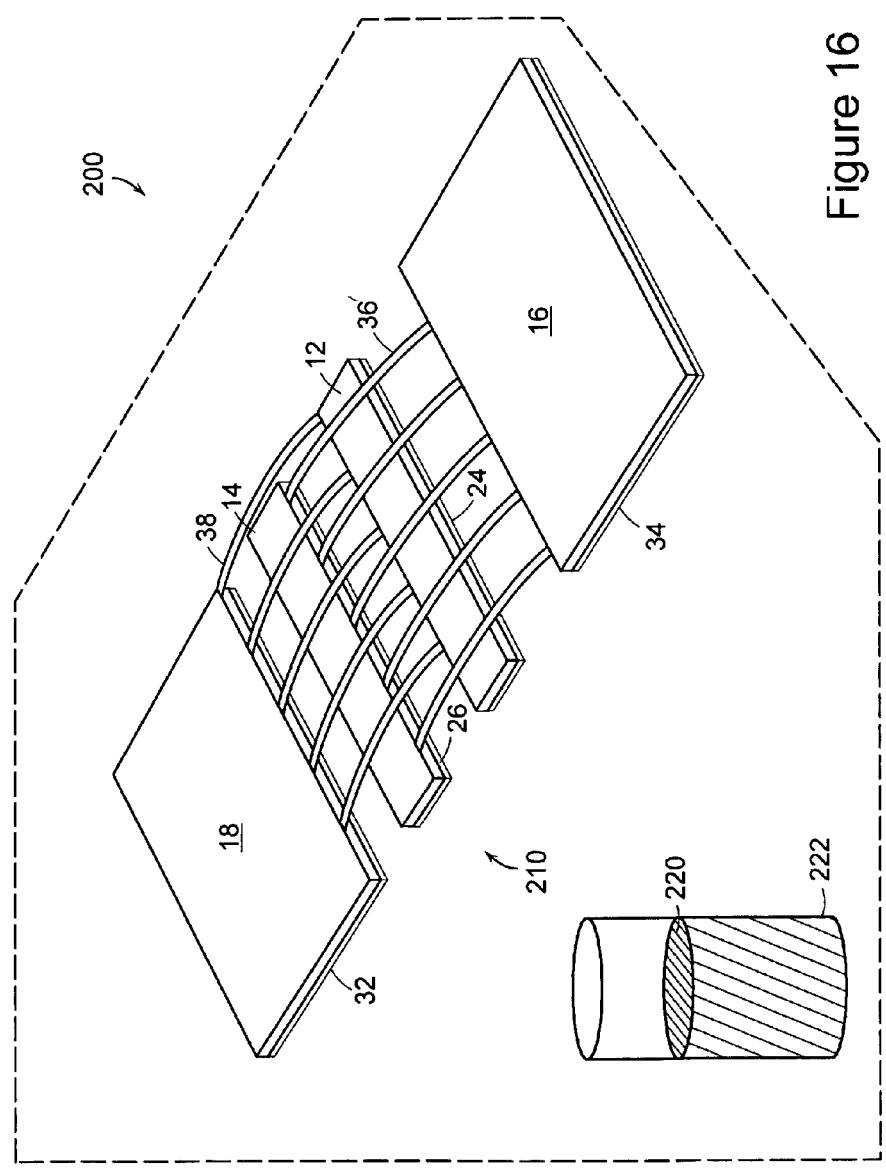
FIG. 16 is a perspective view of a four-component wound closure kit in accordance with a preferred embodiment of the present invention.

FIG. 16 is a perspective view of a four-component wound closure kit 200 in accordance with a preferred embodiment of the present invention. The kit 200 generally includes an interlaced composition that forms a device 210 for closing wound and an adhesive 220 that is adapted for use with the device 210. The adhesive 220 preferably begins in a liquid phase, and is thus optimally contained within a container 222 that may be specially adapted for applying the adhesive 220 to the device 210 during use. For example, the container 222 may be configured with application means, such as a nozzle, a syringe-like tip, or a sponge that allows a user to apply the adhesive 220 in a consistent manner.

The device 210 includes a first wound edge pad 12 and a second wound edge pad 14 that are preferably disposable on either side of a laceration or incision in an individual's skin. The wound edge pads 12, 14 can be comprised of a number of materials known in the art, although a clear and breathable material is preferable in order to permit observation of the wound site and surrounding skin throughout the healing process. Moreover, the material that comprises the wound edge pads 12, 14 can be permeable such that the adhesive 220 can penetrate into the wound edge pads 12, 14 and add rigidity and strength while protecting the wound site.

In preferred embodiments, the wound edge pads 12, 14 are reinforced with a substantially rigid material or scrim, such as a rigid polymer, nylon, or additional layers of semi rigid polymeric materials in order to provide and maintain the dimensional stability of the kit near the wound site during the healing process. Most preferably, the wound edge pads 12, 14 are reinforced along their interior edge, which is defined as the edge placed directly adjacent to the wound during use. Proper reinforcement of the wound edge pads 12, 14 is preferred in order to minimize any torsion or shearing forces that may dislodge the device 210 or traumatize the wound itself.

The wound edge pads 12, 14 are preferably coated with adhesive on one side, or alternatively each of the wound edge pads 12, 14 has an adhesive or glue disposed on its posterior surface (not visible in FIG. 16). In order to maintain the adhesive before application, the first wound edge pad 12 has a first release liner 24 selectively disposed there under; and the second wound edge pad 14 has a second release liner 26 selectively disposed there under. As discussed further herein, the first and second release liners 24, 26 can be selectively removed in order to affix the wound edge pads 12, 14 about the edges of a wound.

The device 210 further includes a first tension adjusting pad 16 and a second tension adjusting pad 18 that are preferably comprised of a material similar or identical to that of the wound edge pads 12, 14. Like the wound edge pads 12, 14, the tension adjusting pads 16, 18 may have adhesive on or have an adhesive or glue disposed on their posterior surfaces (not visible in FIG. 1). However, the tension adjusting pads 16, 18 may also be configured without any adhesive surface, such that they provide tension adjusting through manual means only.

In an embodiment of the present invention in which the tension adjusting pads 16, 18 do have adhesive posterior surfaces, the first tension adjusting pad 16 has a third release liner 34 disposed on its posterior surface; and the second tension adjusting pad 18 has a fourth release liner 32 disposed on its posterior surface. As discussed further herein, the third and fourth release liners 34, 32 can be selectively removed in order to affix the tension adjusting pads 16, 18 to the individual's dermis adjacent to the respective wound edge pads 12, 14. The tension adjusting pads 16, 18 are preferably comprised of a material similar to or identical to the wound edge pads 12, 14.

The device 210 further includes a plurality of elongate connecting elements 38 that connect the first wound edge pad 12 to the second tension adjusting pad 18; as well as a second plurality of elongate connecting elements 36 that connect the second wound edge pad 14 to the first tension adjusting pad 16. The elongate connecting elements 36, 38 can be produced from any flexible, non-elastic material that is securable to the wound edge pads 12, 14 and the tension adjusting pads 16, 18 and can be rendered sterile. Examples of preferred materials for the elongate connecting elements 36, 38 include monofilament or multifilament polymers, extruded films or textiles. The elongate connecting elements 36, 38 may be secured to the wound edge pads 12, 14 and the tension adjusting pads 16, 18 in any conventional means, including for example stitching or adhesion. Alternatively, the elongate connecting elements 36, 38 may be woven, knitted or stitch bonded into a substructure that serves as the foundation for the wound edge pads 12, 14 and the tension adjusting pads 16, 18 construction.

The elongate connecting elements 36, 38 are preferably plural in numbers, such that the tension exerted on the wound edge pads 12, 14 by the tension adjusting pads 16, 18 is substantially uniform in the direction perpendicular to the elongate connecting elements 36, 38. While ten total elongate connecting elements 36, 38 are shown in FIG. 16, it should be understood that this is for illustrative purposes only, and the precise number of elongate connecting elements 36, 38 provided with the kit 200 is a matter of engineering and design choice. Preferably, the elongate connecting elements 36, 38 are sufficient in length such that the tension adjusting pads 16, 18 can be affixed to the individual's skin at least 2 centimeters from the wound itself. More particularly, the elongate connecting elements 36, 38 are preferably between 2 and 5 centimeters in length thus providing a user access to the area between the affixed wound edge pads 12, 14 and tension adjusting pads 16, 18. The elongate connecting elements 36, 38 are preferably composed of a material that is also permeable such that the adhesive 220 can harden therein and add rigidity and strength to the device 210 as a whole.

Figure 17:
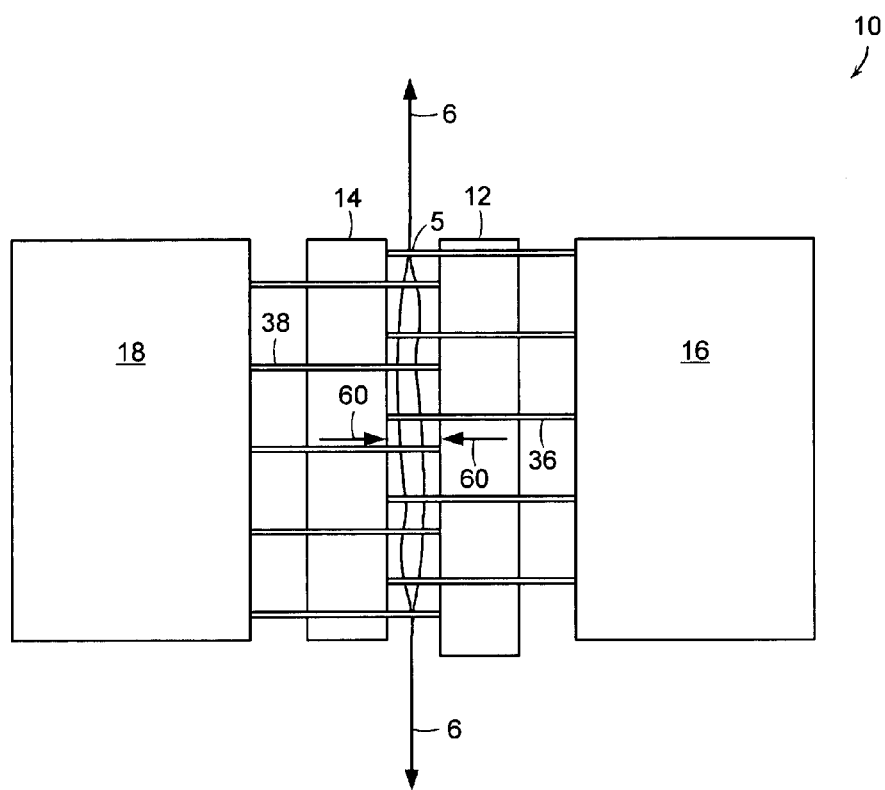
FIG. 17 is a plan view of the wound closure kit illustrated in FIG. 16.

The device 210 is best utilized for closing a wound 5 that is oriented along a longitudinal axis 6, shown in FIG. 17. In use, the device 210 is oriented such that the wound edge pads 12, 14 are deposited adjacent to the wound 5 such that the elongate connecting elements 36, 38 are substantially perpendicular to the longitudinal axis 6. In this manner, the elongate connecting elements 36, 38 serve to maximize the distribution of tension along the length of the wound edge pads 12, 14, which in turn creates a uniform pressure about the edges of the wound 5 in order to speed healing.

Figure 18:
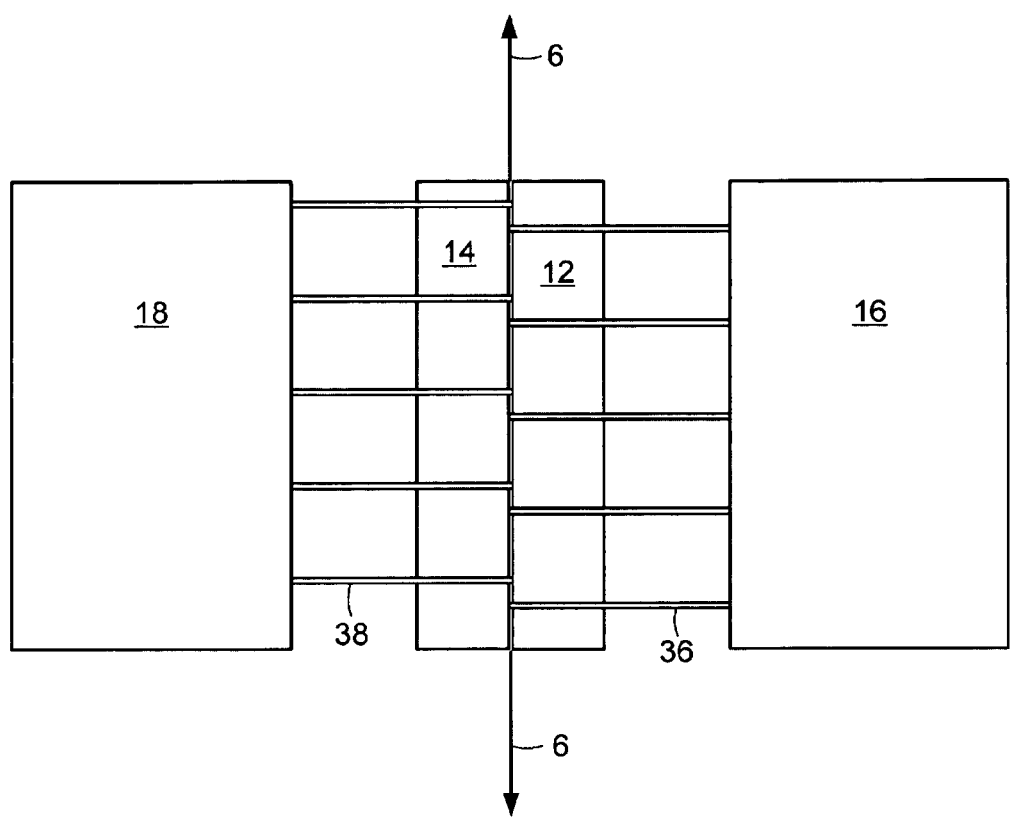
FIG. 18 is a plan view of the wound closure kit in use as illustrated in FIG. 16.

Following removal of the first release liner 24 and the second release liner 26, the wound edge pads 12, 14 are affixed to the individual's skin, the tension adjusting pads 16, 18 are pulled in a direction substantially perpendicular to longitudinal axis 6 as shown in FIG. 18. Once the appropriate tension has been achieved, a user can apply the adhesive 220 to the anterior surface of the wound edge pads 12, 14 and the traversing portions of the elongate connecting elements 36, 38. Alternatively, if the tension adjusting pads 16, 18 are adhesive in nature, then a user can remove the third release liner 34 and the fourth release liner 32 from the tension adjusting pads 16, 18 and affix the same to the individual's skin thus securing the device. In this second instance, the adhesive 220 is utilized to immobilize the wound edge pads 12, 14 relative to each other and relative to the traversing portions of the elongate connecting elements 36, 28.

Figure 19:
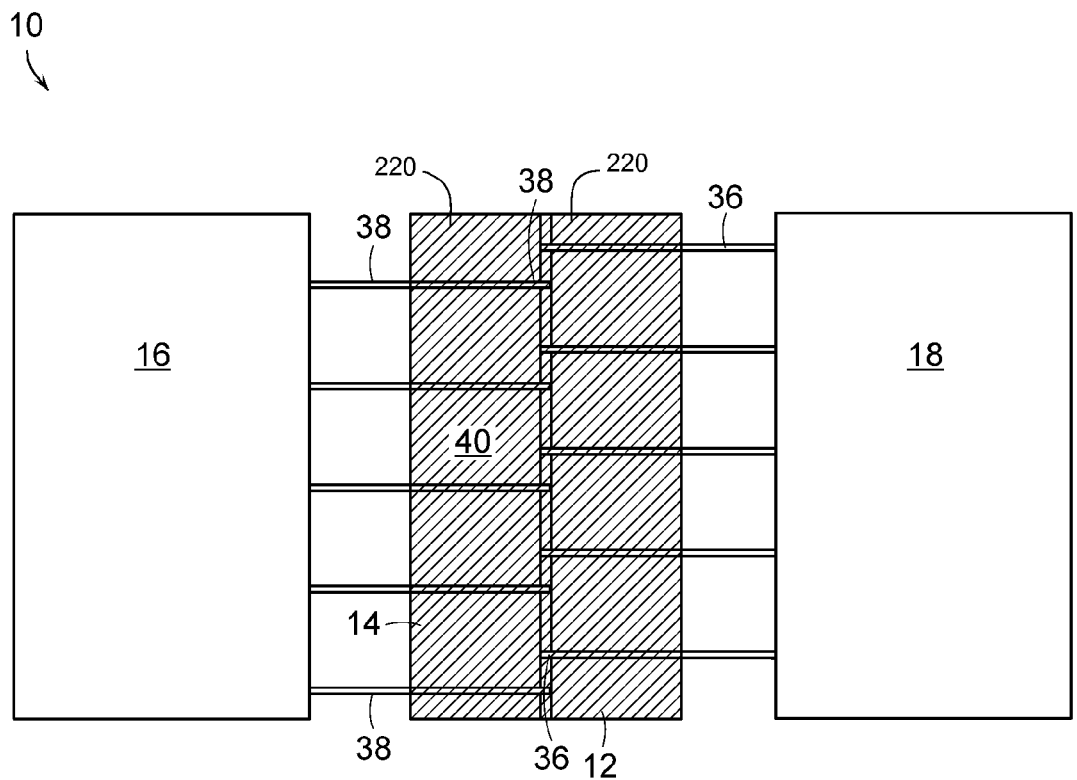
FIG. 19 is a plan view of the wound closure kit in use as illustrated in FIG. 16 including additional features.

FIG. 19 is a plan view of the kit 200 in use following application of the adhesive 220 only to portions of the device 210. As shown herein, the adhesive is applied to the wound site such that it covers only the wound edge pads 12, 14 and those portions of the elongate connecting elements 36, 38 that are disposed there between. The adhesive 220 bonds portions of the elongate connecting elements 36, 38 to the wound edge pads 12, 14 thereby immobilizing the elongate connecting elements 36, 38 and stabilizing the device 210 about the wound 5. The adhesive 220 totally covers the wound edge pads 12, 14 as well as the wound 5 itself. If the user so chooses, the adhesive 220 can be applied to the entire device 210, including the elongate connecting elements 36, 38 and the tension adjusting pads 16, 18. Accordingly, the adhesive 220 further protects the wound 5 from any further trauma, including the introduction of debris or microbial organisms.

Figure 20:
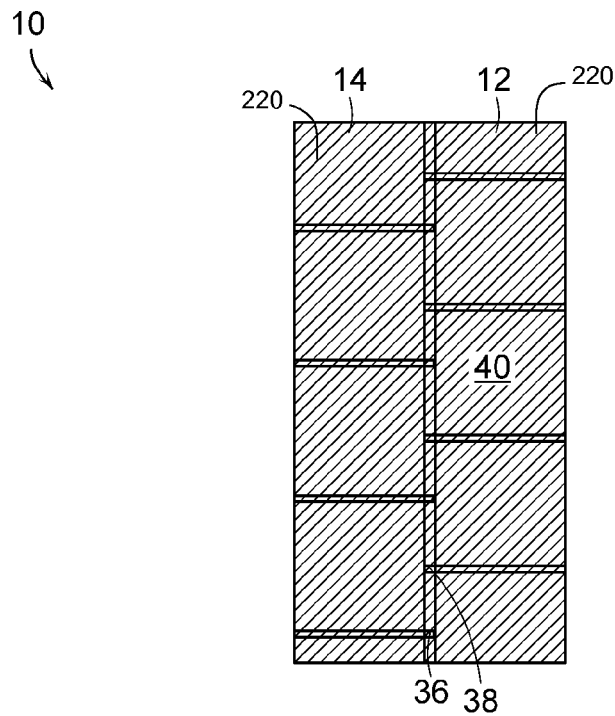
FIG. 20 is a plan view of the wound closure kit in use as illustrated in FIG. 16.

After applying the adhesive 220 to the wound edge pads 12, 14, the exposed portions of the elongate connecting elements 36, 38 can be removed along with the tension adjusting pads 16, 18. Alternatively, if the user so desires the device 210 can be covered by the adhesive in its entirety for enhanced dimensional stability depending on the patient's anatomy. As shown in the plan view of FIG. 20, the kit 200 effectively covers and closes the wound 5 through the placement of the wound edge pads 12, 14 and the adhesive 220. As the elongate connecting elements 36, 38 are removed in this stage of healing, there is a minimal risk that any torsion or shearing force will affect the wound edge pads 12, 14 and aggravate the wound 5. Moreover, as the components of the device 210 may be composed of permeable materials, the adhesion of the adhesive 220 will add additional rigidity and strength to the device 210 during the healing process, further protecting the wound site and the patient from any additional trauma.

The adhesive 220 can be any adhesive known in the medical arts that is well suited for use on human and animal tissues. Examples of a suitable adhesive 220 include evaporative adhesives, polymerizable adhesives and polyurethane-type adhesives. Each of these adhesives operates as a function of water, either through the introduction of water or moisture as a catalyst or through the evaporation of water during the adhering process. Polymerizable adhesives are generally considered the quickest acting of the known adhesives noted above, and are therefore most preferable as an adhesive 220 for purposes of the present invention.

A polymerizable adhesive 220 may include a monomer, dimer, tetramer or a group of polymerizable compounds, such as synthetic or semi-synthetic monomers. Monomers that are readily polymerizable are most preferable, including anionically polymerizable, free radical polymerizable, or polymerizable by zwitterions or ion pairs to form polymers. Although some monomers may be biodegradable, it is not a required feature for purposes of the present invention. The adhesive 220 is preferably hypoallergenic and optimized for use on human or animal tissues, including especially wound sites.

The adhesive 220 is preferably polymerizable for a number of reasons, including for example, the ability to pass through a permeable film thereby increasing the security of wound closure. Additionally, such polymerizable adhesives are known be useful for direct wound closing and therefore any contact with the wound, intentional or otherwise, will not be harmful to the patient.

Suitable monomers for a polymerizable adhesive 220 include 1,1-disubstituted ethylene monomers, such as α-cyanoacrylates. In particular, alkyl α-cyanoacrylates having an alkyl chain including between one and twenty carbon atoms are suitable for purposes of the present invention. The most preferable α-cyanacrylate monomers include: methyl cyanoacrylate, ethyl cyanoacrylate, n-butyl cyanoacrylate, 2-octyl cyanoacrylate, methoxyethyl cyanoacrylate, ethoxyethyl cyanoacrylate, dodeccyleyanoacrylate, 2-ethylhexyl cyanoacrylate, butyl cyanoacrylate, 3-methyoxybutyl cyanoacrylate, 2-butoxyethyl cyanoacrylate, 2-isopropoxyethyl cyanoacrylate, 1-methoxy-2-propyl cyanoacrylate, hexyl cyanoacrylate, or dodecylcyanoacrylate. Other suitable cyanoacrylates for use in the present invention are disclosed in U.S. Pat. No. 6,620,846.

The kit 200 of the present invention is usable according to the steps outlined above. Additionally, it may be preferable to use two or more adhesives 220 of the type described above. Additional substances, such as for example medicaments, can be infused or otherwise added to the adhesives 220 in order to treat and accelerate the healing of the wound. For example, antimicrobial substances such as silver can be also infused or otherwise added into the adhesives 220 in order to reduce any chance of infection to the wound 5. Similarly, medicaments can be introduced into the structure of the device 210 in order to accomplish similar results as noted above.

The kit 200 of the present invention can be used according to a number of methods. In one method, described above, the device 210 is left in place abridging the wound 5 and the adhesive 220 is applied thereto in order to add rigidity and stability to the device 210 during the healing process. Alternatively, the device 210 can be used to align or approximate the wound 5 while the adhesive 220 is being applied. In this method, the wound edge pads 12, 14 are aligned about the wound 5 in the manner described above. Subsequently, the tension adjusting pads 16, 18 are pulled in opposing directions such that the wound edge pads 12, 14 are pulled together about the wound 5 such that wound edge pads 12, 14 will evert the wound 5 edges. In pulling the tension adjusting pads 16, 18, a user will typically be pulling in a direction that is angled relative to the surface upon which the wound 5 is located. In doing so, the elongate connecting elements 36, 38 will form a raised bridge over the wound 5, under which a user may apply the adhesive 220 without touching the device 210.

For example, a user might pull the tension adjusting pads 16, 18 at a forty-five degree angle relative to the wound surface such that the edges of the wound 5 are slightly everted and further such that the elongate connecting elements 36, 38 do not make contact with the wound edge pads 12, 14 and the wound 5 itself. Once the edges of the wound 5 are properly aligned and everted, the user (or a second user) can use the container 222 of the kit 200 to apply the adhesive 220 directly to the wound 5 under the elongate connecting elements 36, 38. The tension applied to the wound edge pads 12, 14 is maintained until the adhesive 220 has sealed or closed the wound 5, after which time the device 210 can be removed about the wound 5, which is now closed and sealed by the adhesive 220.

According to this embodiment of the method of the present invention, it is most preferable that the adhesive 220 be of the polymerizable type described above as it is being applied directly to the wound 5. Suitable polymerizable adhesives, also discussed above, include monomers, dimers, tetramers or a group of polymerizable compounds, such as synthetic or semi-synthetic monomers. Readily polymerizable monomers are most preferable, including especially 1,1-disubstituted ethylene monomers, such as α-cyanoacrylates. The various types of cyanoacrylates that are well suited for the method of the present invention are detailed above.

Although the foregoing description includes references to particular embodiments and methods of manufacture, it should be understood that various alterations could be readily devised by those skilled in the art without departing from the scope of the present invention as defined by the following claims.

What is claimed is:

1. A wound closure kit comprising:
   a) A device comprising a first and a second interlaced component, each of the first and second interlaced components comprising:
      i) an adhesive-backed wound edge pad for attachment to the skin of an individual adjacent a wound to be closed, the adhesive-backed pad of the first interlaced component being applied along a first side of the wound and the adhesive-backed pad of the second interlaced component being applied along a second side of the wound;
      ii) a tension adjusting pad;
      iii) elongate connecting elements joining the adhesive-backed wound edge pad to the tension adjusting pad; and
   b) an adhesive composition affixed to portions of the elongate connecting elements and adjacent adhesive-backed wound edge pads to which the adhesive composition is applied following initial application of the interlaced components and wound closure, the adhesion of the adhesive composition functioning to attach only the portions of the elongate connectors overlying the adhesive-backed wound edge pads to the wound edge pads thereby immobilizing the elongate connecting elements against the wound edge pads and stabilizing the wound edge pads relative to each other and relative to the traversing portions of the elongate connecting elements and maintaining closure of the wound and effectively limiting any torsion or shearing forces that may dislodge the wound edge pads relative to each other, wherein exposed, adhesive-free portions of the elongate connecting elements and associated tensioning pads, are adapted for removal following adhesion of the adhesive composition.

2. The wound closure kit of claim 1 wherein the adhesive composition is a polymerizable adhesive composition.

3. The wound closure kit of claim 2 wherein the wound edge pads are comprised of a permeable material such that the polymerizable adhesive composition permeates the wound edge pads.

4. The wound closure kit of claim 2 wherein the elongate connecting elements are comprised of a permeable material such that the polymerizable adhesive composition permeates the elongate connecting elements.

5. The wound closure kit of claim 2 wherein the polymerizable adhesive composition is polymerized shortly after application to the wound edge pads.

6. The wound closure kit of claim 2 wherein the polymerizable adhesive composition is one of a monomer, a dimer, or a tetramer.

7. The wound closure kit of claim 2 wherein the polymerizable adhesive composition is a monomer.

8. The wound closure kit of claim 2 wherein the polymerizable adhesive composition is a 1,1-disubstituted monomer.

9. The wound closure kit of claim 2 wherein the polymerizable adhesive composition is a cyanoacrylate monomer.

10. The wound closure kit of claim 1 wherein the tension adjusting pads are adhesive-backed.

11. The wound closure kit of claim 1 further comprising a second adhesive composition.

12. The wound closure kit of claim 1 wherein the adhesive composition includes a microbial ingredient for reducing the possibility of infection to the wound.

13. The wound closure kit of claim 1 wherein the elongate connecting elements are sufficiently spaced-apart to facilitate lateral adjustment of the adhesive-backed wound edge pad of the first interlaced component relative to the adhesive-backed wound edge pad of the second interlaced component.

14. The wound closure kit of claim 1 wherein the edge of each of the wound edge pads that is applied nearest to and substantially parallel to the wound to be closed is reinforced with a substantially rigid material.

15. The wound closure kit of claim 14 wherein the substantially rigid material is a scrim.

16. The wound closure kit of claim 1 wherein the wound edge pads are produced from a substantially transparent, breathable substrate.

17. The wound closure kit of claim 1 wherein the tension adjusting pads are produced from a substantially transparent, breathable material.

18. The wound closure kit of claim 1 wherein the elongate connectors, the wound edge pads and the tension adjusting pads are produced from a substantially inelastic stock.

19. The wound closure kit of claim 18 wherein the elongate connectors, the wound edge pads and the tension adjusting pads are reinforced with scrims.

20. The wound closure kit of claim 1 wherein the elongate connectors, the wound edge pads and the tension adjusting pads are reinforced by mating with a substantially inelastic material.

21. The wound closure kit of claim 1 wherein the wound edge pads adjacent to the wound edges are adapted to evert the skin edges.

22. The wound closure kit of claim 1 wherein the components are adapted for wound edge alignment of the wound edge pads.

23. The wound closure kit of claim 1 wherein the components are adapted for transdermal drug delivery.

24. The wound closure kit of claim 1 wherein the components are adapted for measuring tension applied to the wound edge pads during closing.

25. The wound closure kit of claim 1 further comprising a substructure upon which the adhesive is disposed to form the adhesive-backed wound edge pads and the tensioning pads.

26. The would closure kit of claim 25 wherein the substructure is comprised of a textile material.

27. The wound closure kit of claim 25 wherein the substructure is comprised of a polymeric material.

28. The wound closure kit of claim 25 wherein the substructure is comprised of a woven material.

29. The wound closure kit of claim 25 wherein the substructure is comprised of a non-woven material.

* * * * *